United States Patent
Yee et al.

(10) Patent No.: US 12,402,883 B2
(45) Date of Patent: Sep. 2, 2025

(54) SURGICAL INSTRUMENT WITH LINEAR AND PURSE STRING SUTURE STAPLES

(71) Applicant: INTUITIVE SURGICAL OPERATIONS, INC., Sunnyvale, CA (US)

(72) Inventors: Kristopher Yee, San Jose, CA (US); Emily Cooper, San Francisco, CA (US); Heath Corbet, Campbell, CA (US); Charles Godin, Palo Alto, CA (US); Paul Millman, Denver, CO (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 109 days.

(21) Appl. No.: 18/271,432

(22) PCT Filed: Dec. 28, 2021

(86) PCT No.: PCT/US2021/065308
§ 371 (c)(1),
(2) Date: Jul. 7, 2023

(87) PCT Pub. No.: WO2022/150212
PCT Pub. Date: Jul. 14, 2022

(65) Prior Publication Data
US 2024/0350143 A1    Oct. 24, 2024

Related U.S. Application Data

(60) Provisional application No. 63/134,961, filed on Jan. 8, 2021.

(51) Int. Cl.
*A61B 17/115* (2006.01)
*A61B 17/11* (2006.01)
*A61B 17/3209* (2006.01)

(52) U.S. Cl.
CPC ......... *A61B 17/115* (2013.01); *A61B 17/1114* (2013.01); *A61B 17/3209* (2013.01); *A61B 2017/1142* (2013.01)

(58) Field of Classification Search
CPC ... A61B 17/115; A61B 17/105; A61B 17/068; A61B 17/072
See application file for complete search history.

(56) References Cited

U.S. PATENT DOCUMENTS

| | | | |
|---|---|---|---|
| 75,364 | A | 3/1868 | Case |
| 3,792,597 | A | 2/1974 | Orain et al. |

(Continued)

FOREIGN PATENT DOCUMENTS

| | | |
|---|---|---|
| CN | 103889344 A | 6/2014 |
| CN | 104042275 A | 9/2014 |

(Continued)

OTHER PUBLICATIONS

Anonymous: "Slip Joint Pliers—Wikipedia," Sep. 2017, 1 Pages. Retrieved from internet URL:https://en.wikipedia.org/w/index.php?tilte=split_joint_pliers&oldid=801407143.

(Continued)

*Primary Examiner* — Nathaniel C Chukwurah
(74) *Attorney, Agent, or Firm* — Farber LLC

(57) ABSTRACT

A surgical stapling instrument is configured to dissect tissue, apply a linear staple line along one side of the tissue dissection and apply a suture, such as a purse string suture, to the other side of the tissue dissection. The instrument comprises an elongate shaft, first and second jaws configured to open and close and a cutting element. The instrument includes a first row of staples in each of the first and second jaws having a suture extending therethrough and a second row of staples in the second jaw. A drive member is configured to translate distally through the end effector to (Continued)

dissect tissue with the cutting element, drive the second row of staples into the tissue on one side of the dissection and to apply the first row of staples and suture in combination to form a purse string suture on the other side of the tissue dissection.

20 Claims, 25 Drawing Sheets

(56) References Cited

U.S. PATENT DOCUMENTS

| | | | |
|---|---|---|---|
| 4,305,539 A | 12/1981 | Korolkov et al. | |
| 4,319,576 A | 3/1982 | Rothfuss | |
| 4,352,276 A | 10/1982 | Smith | |
| 4,403,892 A | 9/1983 | Kane | |
| 4,407,286 A | 10/1983 | Noiles et al. | |
| 4,429,695 A | 2/1984 | Green | |
| 4,509,518 A | 4/1985 | McGarry et al. | |
| 4,509,932 A | 4/1985 | Weible | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,874 A | 1/1987 | Chow et al. | |
| 4,767,044 A | 8/1988 | Green | |
| 4,809,695 A | 3/1989 | Gwathmey | |
| 4,848,637 A | 7/1989 | Pruitt | |
| 4,892,244 A | 1/1990 | Fox et al. | |
| 4,930,503 A | 6/1990 | Pruitt | |
| 4,978,049 A | 12/1990 | Green | |
| 5,007,300 A | 4/1991 | Siva | |
| 5,027,834 A | 7/1991 | Pruitt | |
| 5,040,715 A | 8/1991 | Green et al. | |
| 5,133,735 A | 7/1992 | Slater et al. | |
| 5,133,736 A | 7/1992 | Bales, Jr. et al. | |
| 5,142,931 A | 9/1992 | Menahem | |
| 5,147,357 A | 9/1992 | Rose et al. | |
| 5,180,092 A | 1/1993 | Crainich | |
| 5,242,457 A * | 9/1993 | Akopov | A61B 17/1114 606/220 |
| 5,275,323 A | 1/1994 | Schulze et al. | |
| 5,307,976 A | 5/1994 | Olson et al. | |
| 5,312,023 A | 5/1994 | Green et al. | |
| 5,316,435 A | 5/1994 | Mozingo | |
| 5,334,183 A | 8/1994 | Wuchinich | |
| 5,342,395 A | 8/1994 | Jarrett et al. | |
| 5,342,396 A | 8/1994 | Cook | |
| 5,366,133 A | 11/1994 | Geiste | |
| 5,452,836 A | 9/1995 | Huitema et al. | |
| 5,452,837 A | 9/1995 | Williamson, IV et al. | |
| 5,465,895 A | 11/1995 | Knodel et al. | |
| 5,480,089 A | 1/1996 | Blewett | |
| 5,484,095 A | 1/1996 | Green et al. | |
| 5,484,451 A | 1/1996 | Akopov et al. | |
| 5,487,500 A | 1/1996 | Knodel et al. | |
| 5,497,931 A | 3/1996 | Nakamura | |
| 5,533,521 A | 7/1996 | Granger | |
| 5,540,375 A | 7/1996 | Bolanos et al. | |
| 5,554,164 A | 9/1996 | Wilson et al. | |
| 5,560,530 A | 10/1996 | Bolanos et al. | |
| 5,562,239 A | 10/1996 | Boiarski et al. | |
| 5,564,615 A | 10/1996 | Bishop et al. | |
| 5,571,116 A | 11/1996 | Bolanos et al. | |
| 5,571,285 A | 11/1996 | Chow et al. | |
| 5,573,534 A | 11/1996 | Stone | |
| 5,573,543 A * | 11/1996 | Akopov | A61B 17/04 227/176.1 |
| 5,607,449 A | 3/1997 | Tontarra | |
| 5,615,820 A | 4/1997 | Viola | |
| 5,624,452 A | 4/1997 | Yates | |
| 5,628,446 A | 5/1997 | Geiste et al. | |
| 5,632,432 A | 5/1997 | Schulze et al. | |
| 5,651,491 A | 7/1997 | Heaton et al. | |
| 5,652,849 A | 7/1997 | Conway et al. | |
| 5,667,626 A | 9/1997 | Cayford et al. | |
| 5,673,840 A | 10/1997 | Schulze et al. | |
| 5,673,842 A | 10/1997 | Bittner et al. | |
| 5,676,674 A | 10/1997 | Bolanos et al. | |
| 5,688,269 A | 11/1997 | Newton et al. | |
| 5,690,269 A | 11/1997 | Bolanos et al. | |
| 5,693,042 A | 12/1997 | Boiarski et al. | |
| 5,697,542 A | 12/1997 | Knodel et al. | |
| 5,700,270 A | 12/1997 | Peyser et al. | |
| 5,700,276 A | 12/1997 | Benecke | |
| 5,704,534 A | 1/1998 | Huitema et al. | |
| 5,709,680 A | 1/1998 | Yates et al. | |
| 5,738,474 A | 4/1998 | Blewett | |
| 5,752,644 A | 5/1998 | Bolanos et al. | |
| 5,752,973 A | 5/1998 | Kieturakis et al. | |
| 5,762,255 A | 6/1998 | Chrisman et al. | |
| 5,762,256 A | 6/1998 | Mastri et al. | |
| 5,779,130 A | 7/1998 | Alesi et al. | |
| 5,782,396 A | 7/1998 | Mastri et al. | |
| 5,792,135 A | 8/1998 | Madhani et al. | |
| 5,820,009 A | 10/1998 | Melling et al. | |
| 5,826,776 A | 10/1998 | Schulze et al. | |
| 5,833,695 A | 11/1998 | Yoon | |
| 5,865,361 A | 2/1999 | Milliman et al. | |
| 5,871,135 A | 2/1999 | Williamson, IV et al. | |
| 5,911,353 A | 6/1999 | Bolanos et al. | |
| 5,915,616 A | 6/1999 | Viola et al. | |
| 5,919,198 A | 7/1999 | Graves, Jr. et al. | |
| 5,941,442 A | 8/1999 | Geiste et al. | |
| 5,954,259 A | 9/1999 | Viola et al. | |
| 5,959,892 A | 9/1999 | Lin et al. | |
| 6,032,849 A | 3/2000 | Mastri et al. | |
| 6,050,996 A | 4/2000 | Schmaltz et al. | |
| 6,079,606 A | 6/2000 | Milliman et al. | |
| 6,113,598 A | 9/2000 | Baker | |
| 6,126,666 A | 10/2000 | Trapp et al. | |
| 6,174,309 B1 | 1/2001 | Wrublewski et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,312,426 B1 | 11/2001 | Goldberg et al. | |
| 6,330,956 B1 | 12/2001 | Willinger | |
| 6,330,965 B1 | 12/2001 | Milliman et al. | |
| 6,488,196 B1 | 12/2002 | Fenton, Jr. | |
| 6,503,259 B2 | 1/2003 | Huxel et al. | |
| 6,582,451 B1 | 6/2003 | Marucci et al. | |
| 6,585,735 B1 | 7/2003 | Frazier et al. | |
| 6,644,532 B2 | 11/2003 | Green et al. | |
| 6,656,193 B2 | 12/2003 | Grant et al. | |
| 6,669,073 B2 | 12/2003 | Milliman et al. | |
| 6,692,363 B1 | 2/2004 | Heutschi et al. | |
| 6,770,072 B1 | 8/2004 | Truckai et al. | |
| 6,786,382 B1 | 9/2004 | Hoffman | |
| 6,817,974 B2 | 11/2004 | Cooper et al. | |
| 6,840,938 B1 | 1/2005 | Morley et al. | |
| 6,877,647 B2 | 4/2005 | Green et al. | |
| 6,905,057 B2 | 6/2005 | Swayze et al. | |
| 6,953,139 B2 | 10/2005 | Milliman et al. | |
| 6,955,608 B1 | 10/2005 | Lutz | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,985,133 B1 | 1/2006 | Rodomista et al. | |
| 6,986,451 B1 | 1/2006 | Mastri et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,114,642 B2 | 10/2006 | Whitman | |
| 7,128,253 B2 | 10/2006 | Mastri et al. | |
| 7,140,527 B2 | 11/2006 | Ehrenfels et al. | |
| 7,140,528 B2 | 11/2006 | Shelton, IV et al. | |
| 7,258,262 B2 | 8/2007 | Mastri et al. | |
| 7,296,722 B2 | 11/2007 | Ivanko | |
| 7,308,998 B2 | 12/2007 | Mastri et al. | |

(56) References Cited

U.S. PATENT DOCUMENTS

| | | |
|---|---|---|
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,491,202 B2 | 2/2009 | Odom et al. |
| 7,494,039 B2 | 2/2009 | Racenet et al. |
| 7,561,141 B2 | 7/2009 | Shahoian et al. |
| 7,565,993 B2 | 7/2009 | Milliman et al. |
| 7,588,174 B2 | 9/2009 | Holsten et al. |
| 7,654,431 B2 | 2/2010 | Hueil et al. |
| 7,658,312 B2 | 2/2010 | Vidal et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,780,577 B2 | 8/2010 | Arnold |
| 7,794,475 B2 | 9/2010 | Hess et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,439,246 B1 | 5/2013 | Knodel |
| 8,490,851 B2 | 7/2013 | Blier et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,206 B2 | 3/2014 | Aranyi et al. |
| 8,672,939 B2 | 3/2014 | Garrison |
| 8,701,960 B1 | 4/2014 | Manoux et al. |
| 8,783,541 B2 | 7/2014 | Shelton, IV et al. |
| 8,800,841 B2 | 8/2014 | Ellerhorst et al. |
| 8,834,518 B2 | 9/2014 | Faller et al. |
| 8,851,355 B2 | 10/2014 | Aranyi et al. |
| 8,852,174 B2 | 10/2014 | Burbank |
| 8,858,547 B2 | 10/2014 | Brogna |
| 8,864,010 B2 | 10/2014 | Williams |
| 8,876,857 B2 | 11/2014 | Burbank |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,016,545 B2 | 4/2015 | Aranyi et al. |
| 9,055,961 B2 | 6/2015 | Manzo et al. |
| 9,161,807 B2 | 10/2015 | Garrison |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,307,986 B2 | 4/2016 | Hall et al. |
| 9,316,267 B2 | 4/2016 | Lenz et al. |
| 9,345,479 B2 | 5/2016 | Racenet et al. |
| 9,498,215 B2 | 11/2016 | Duque et al. |
| 9,717,497 B2 | 8/2017 | Zerkle et al. |
| 9,717,498 B2 | 8/2017 | Aranyi et al. |
| 9,777,459 B2 | 10/2017 | Zuritis |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,231,733 B2 | 3/2019 | Ehrenfels et al. |
| 10,285,693 B2 | 5/2019 | Kimsey et al. |
| 10,335,147 B2 | 7/2019 | Rector et al. |
| 10,363,037 B2 | 7/2019 | Aronhalt et al. |
| 10,646,219 B2 | 5/2020 | Racenet et al. |
| 10,722,233 B2 | 7/2020 | Wellman |
| 10,828,027 B2 | 11/2020 | Racenet et al. |
| 10,863,988 B2 | 12/2020 | Patel et al. |
| 10,912,556 B2 | 2/2021 | Burbank |
| 10,973,517 B2 | 4/2021 | Wixey |
| 11,020,138 B2 | 6/2021 | Ragosta |
| 11,166,773 B2 | 11/2021 | Ragosta et al. |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 11,607,219 B2 | 3/2023 | Shelton, IV et al. |
| 11,642,129 B2 | 5/2023 | Burbank |
| 11,696,758 B2 | 7/2023 | Murphy et al. |
| 11,723,661 B2 | 8/2023 | Wixey et al. |
| 11,759,202 B2 | 9/2023 | Morgan et al. |
| 11,786,325 B2 | 10/2023 | Mustufa et al. |
| 11,806,015 B2 | 11/2023 | Wixey et al. |
| 11,857,188 B2 | 1/2024 | Hites |
| 11,864,762 B2 | 1/2024 | Wixey |
| 11,896,224 B2 | 2/2024 | Wellman |
| 11,903,583 B2 | 2/2024 | Burbank et al. |
| 11,944,301 B2 | 4/2024 | Wixey et al. |
| 11,944,302 B2 | 4/2024 | Wixey et al. |
| 11,986,184 B2 | 5/2024 | Patel et al. |
| 12,000,280 B2 | 6/2024 | King |
| 12,011,168 B2 | 6/2024 | Wixey |
| 12,029,426 B2 | 7/2024 | Millman et al. |
| 12,029,473 B2 | 7/2024 | Whitlock et al. |
| 12,089,844 B2 | 9/2024 | Patel et al. |
| 12,137,903 B2 | 11/2024 | Patel et al. |
| 12,156,654 B2 | 12/2024 | Wellman |
| 2002/0165562 A1 | 11/2002 | Grant et al. |
| 2002/0177843 A1 | 11/2002 | Anderson et al. |
| 2002/0188293 A1 | 12/2002 | Manzo |
| 2002/0188294 A1 | 12/2002 | Couture et al. |
| 2003/0078577 A1 | 4/2003 | Truckai et al. |
| 2003/0135204 A1 | 7/2003 | Lee et al. |
| 2003/0144652 A1 | 7/2003 | Baker et al. |
| 2003/0171747 A1 | 9/2003 | Kanehira et al. |
| 2003/0181910 A1 | 9/2003 | Dycus et al. |
| 2004/0006340 A1 | 1/2004 | Latterell et al. |
| 2004/0049185 A1 | 3/2004 | Latterell et al. |
| 2004/0143263 A1 | 7/2004 | Schechter et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0021027 A1 | 1/2005 | Shields et al. |
| 2005/0070925 A1 | 3/2005 | Shelton, IV et al. |
| 2005/0070958 A1 | 3/2005 | Swayze et al. |
| 2005/0101991 A1 | 5/2005 | Ahlberg et al. |
| 2005/0113826 A1 | 5/2005 | Johnson et al. |
| 2005/0171533 A1 | 8/2005 | Latterell et al. |
| 2005/0178813 A1 | 8/2005 | Swayze et al. |
| 2005/0187576 A1 | 8/2005 | Whitman et al. |
| 2005/0273084 A1 | 12/2005 | Hinman et al. |
| 2005/0273085 A1 | 12/2005 | Hinman et al. |
| 2006/0000868 A1 | 1/2006 | Shelton, IV et al. |
| 2006/0016853 A1 | 1/2006 | Racenet |
| 2006/0020287 A1 | 1/2006 | Lee et al. |
| 2006/0022014 A1 | 2/2006 | Shelton, IV et al. |
| 2006/0022015 A1 | 2/2006 | Shelton, IV et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 | 5/2006 | Hinman et al. |
| 2006/0111210 A1 | 5/2006 | Hinman |

(56) References Cited

U.S. PATENT DOCUMENTS

| | | |
|---|---|---|
| 2006/0124689 A1 | 6/2006 | Arad et al. |
| 2006/0161190 A1 | 7/2006 | Gadberry et al. |
| 2006/0190031 A1 | 8/2006 | Wales et al. |
| 2006/0199999 A1 | 9/2006 | Ikeda et al. |
| 2006/0217706 A1 | 9/2006 | Lau et al. |
| 2006/0217709 A1 | 9/2006 | Couture et al. |
| 2006/0271042 A1 | 11/2006 | Latterell et al. |
| 2007/0010838 A1 | 1/2007 | Shelton, IV et al. |
| 2007/0045379 A1 | 3/2007 | Shelton, IV |
| 2007/0250113 A1 | 10/2007 | Hegeman et al. |
| 2007/0262116 A1 | 11/2007 | Hueil et al. |
| 2008/0023522 A1 | 1/2008 | Olson et al. |
| 2008/0029577 A1 | 2/2008 | Shelton et al. |
| 2008/0064572 A1 | 3/2008 | Nardone |
| 2008/0065100 A1 | 3/2008 | Larkin |
| 2008/0078804 A1 | 4/2008 | Shelton et al. |
| 2008/0086114 A1 | 4/2008 | Schmitz et al. |
| 2008/0093517 A1 | 4/2008 | Chen |
| 2008/0108446 A1 | 5/2008 | Faude |
| 2008/0161174 A1 | 7/2008 | Lo |
| 2008/0196533 A1 | 8/2008 | Bergamasco et al. |
| 2008/0210738 A1 | 9/2008 | Shelton et al. |
| 2008/0280736 A1 | 11/2008 | D'Eredita |
| 2008/0305934 A1 | 12/2008 | Medina |
| 2008/0308607 A1 | 12/2008 | Timm et al. |
| 2009/0181832 A1 | 7/2009 | Bell |
| 2009/0277947 A1 | 11/2009 | Viola |
| 2010/0006620 A1 | 1/2010 | Sorrentino et al. |
| 2010/0009818 A1 | 1/2010 | Simonson et al. |
| 2010/0057081 A1 | 3/2010 | Hanna |
| 2010/0057085 A1 | 3/2010 | Holcomb et al. |
| 2010/0076461 A1 | 3/2010 | Viola et al. |
| 2010/0076474 A1 | 3/2010 | Yates et al. |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0213240 A1 | 8/2010 | Kostrzewski |
| 2010/0331857 A1 | 12/2010 | Doyle et al. |
| 2011/0022078 A1 | 1/2011 | Hinman |
| 2011/0036891 A1 | 2/2011 | Zemlok et al. |
| 2011/0087238 A1 | 4/2011 | Wang et al. |
| 2011/0118707 A1 | 5/2011 | Burbank |
| 2011/0118778 A1 | 5/2011 | Burbank |
| 2011/0121050 A1 | 5/2011 | Nicholas et al. |
| 2011/0152879 A1 | 6/2011 | Williams |
| 2011/0174863 A1 | 7/2011 | Shelton, IV et al. |
| 2011/0186614 A1 | 8/2011 | Kasvikis |
| 2011/0251612 A1 | 10/2011 | Faller et al. |
| 2011/0251613 A1 | 10/2011 | Guerra et al. |
| 2011/0282339 A1 | 11/2011 | Weizman et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2011/0319886 A1 | 12/2011 | Chojin et al. |
| 2012/0000962 A1 | 1/2012 | Racenet et al. |
| 2012/0022584 A1 | 1/2012 | Donnigan et al. |
| 2012/0071891 A1 | 3/2012 | Itkowitz et al. |
| 2012/0205419 A1 | 8/2012 | Weir et al. |
| 2012/0209253 A1 | 8/2012 | Donhowe |
| 2012/0223121 A1 | 9/2012 | Viola et al. |
| 2012/0228358 A1 | 9/2012 | Zemlok et al. |
| 2012/0248167 A1 | 10/2012 | Flanagan et al. |
| 2012/0255986 A1 | 10/2012 | Petty et al. |
| 2012/0289999 A1 | 11/2012 | Frank |
| 2012/0298719 A1 | 11/2012 | Shelton, IV et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0075448 A1 | 3/2013 | Schmid et al. |
| 2013/0087599 A1 | 4/2013 | Krumanaker et al. |
| 2013/0098965 A1 | 4/2013 | Kostrzewski et al. |
| 2013/0126586 A1 | 5/2013 | Zhang et al. |
| 2013/0148577 A1 | 6/2013 | Terry et al. |
| 2013/0240604 A1 | 9/2013 | Knodel |
| 2013/0248577 A1 | 9/2013 | Leimbach et al. |
| 2013/0277410 A1 | 10/2013 | Fernandez et al. |
| 2013/0296922 A1 | 11/2013 | Allen, IV et al. |
| 2013/0327808 A1 | 12/2013 | Chen et al. |
| 2014/0001236 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0005662 A1 | 1/2014 | Shelton, IV |
| 2014/0021239 A1 | 1/2014 | Kostrzewski |
| 2014/0025071 A1 | 1/2014 | Sims et al. |
| 2014/0027492 A1 | 1/2014 | Williams |
| 2014/0100569 A1 | 4/2014 | Lawes et al. |
| 2014/0100600 A1 | 4/2014 | Kendrick |
| 2014/0103093 A1 | 4/2014 | Koch, Jr. et al. |
| 2014/0110455 A1 | 4/2014 | Ingmanson et al. |
| 2014/0131418 A1* | 5/2014 | Kostrzewski .... A61B 17/07292 227/176.1 |
| 2014/0175152 A1 | 6/2014 | Hess et al. |
| 2014/0180286 A1 | 6/2014 | Marczyk et al. |
| 2014/0183244 A1 | 7/2014 | Duque et al. |
| 2014/0200596 A1 | 7/2014 | Weir et al. |
| 2014/0200612 A1 | 7/2014 | Weir et al. |
| 2014/0200851 A1 | 7/2014 | Weir et al. |
| 2014/0214049 A1 | 7/2014 | Jeong et al. |
| 2014/0239036 A1 | 8/2014 | Zerkle et al. |
| 2014/0239044 A1 | 8/2014 | Hoffman |
| 2014/0239046 A1 | 8/2014 | Milliman et al. |
| 2014/0246477 A1 | 9/2014 | Koch, Jr. et al. |
| 2014/0249557 A1 | 9/2014 | Koch, Jr. et al. |
| 2014/0257331 A1 | 9/2014 | Kim et al. |
| 2014/0263546 A1 | 9/2014 | Aranyi |
| 2014/0263552 A1 | 9/2014 | Hall et al. |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0276731 A1 | 9/2014 | Voegele et al. |
| 2014/0276776 A1 | 9/2014 | Parihar et al. |
| 2014/0284372 A1 | 9/2014 | Kostrzewski |
| 2014/0305989 A1 | 10/2014 | Parihar et al. |
| 2014/0309666 A1 | 10/2014 | Shelton, IV et al. |
| 2014/0343550 A1 | 11/2014 | Faller et al. |
| 2014/0343569 A1 | 11/2014 | Turner |
| 2014/0364851 A1 | 12/2014 | Batross et al. |
| 2015/0018856 A1 | 1/2015 | Poo et al. |
| 2015/0073746 A1 | 3/2015 | Gris et al. |
| 2015/0088131 A1 | 3/2015 | Weisshaupt et al. |
| 2015/0141981 A1 | 5/2015 | Price et al. |
| 2015/0141993 A1 | 5/2015 | Schechter et al. |
| 2015/0173756 A1 | 6/2015 | Baxter, III et al. |
| 2015/0173789 A1 | 6/2015 | Baxter, III et al. |
| 2015/0209030 A1 | 7/2015 | Kostrzewski et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272575 A1 | 10/2015 | Leimbach et al. |
| 2015/0272576 A1 | 10/2015 | Cappola |
| 2015/0272583 A1 | 10/2015 | Leimbach et al. |
| 2015/0272606 A1 | 10/2015 | Nobis |
| 2015/0297227 A1 | 10/2015 | Huitema et al. |
| 2015/0297230 A1 | 10/2015 | Schellin et al. |
| 2015/0297235 A1 | 10/2015 | Harris et al. |
| 2015/0316431 A1 | 11/2015 | Collins et al. |
| 2015/0369277 A1 | 12/2015 | Fevre et al. |
| 2015/0374396 A1 | 12/2015 | Strobl et al. |
| 2016/0038227 A1 | 2/2016 | Garrison |
| 2016/0058441 A1 | 3/2016 | Morgan et al. |
| 2016/0058450 A1 | 3/2016 | Shelton, IV et al. |
| 2016/0066916 A1 | 3/2016 | Overmyer et al. |
| 2016/0089148 A1 | 3/2016 | Harris et al. |
| 2016/0120544 A1 | 5/2016 | Shelton, IV et al. |
| 2016/0157863 A1 | 6/2016 | Williams et al. |
| 2016/0174973 A1 | 6/2016 | Shelton, IV et al. |
| 2016/0174977 A1 | 6/2016 | Lytle, IV et al. |
| 2016/0175033 A1 | 6/2016 | Le |
| 2016/0192999 A1 | 7/2016 | Stulen et al. |

(56) References Cited

U.S. PATENT DOCUMENTS

| | | |
|---|---|---|
| 2016/0199124 A1 | 7/2016 | Thomas et al. |
| 2016/0235473 A1 | 8/2016 | Hagland |
| 2016/0235489 A1 | 8/2016 | Gombert et al. |
| 2016/0242782 A1 | 8/2016 | Shelton, IV et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0287316 A1 | 10/2016 | Worrell et al. |
| 2016/0296226 A1 | 10/2016 | Kostrzewski |
| 2016/0317216 A1 | 11/2016 | Hermes et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0056098 A1 | 3/2017 | Crews et al. |
| 2017/0065331 A1 | 3/2017 | Mayer et al. |
| 2017/0079710 A1 | 3/2017 | Deville et al. |
| 2017/0097035 A1 | 4/2017 | Zimmerman et al. |
| 2017/0105754 A1 | 4/2017 | Boudreaux et al. |
| 2017/0135746 A1 | 5/2017 | Tetzlaff et al. |
| 2017/0143335 A1 | 5/2017 | Gupta et al. |
| 2017/0156788 A1 | 6/2017 | Johnson et al. |
| 2017/0189028 A1 | 7/2017 | Aranyi |
| 2017/0231853 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1 | 1/2018 | Hatanaka et al. |
| 2018/0021042 A1 | 1/2018 | Nicholas et al. |
| 2018/0078268 A1 | 3/2018 | Messerly et al. |
| 2018/0125570 A1 | 5/2018 | Rioux |
| 2018/0161052 A1 | 6/2018 | Weir et al. |
| 2018/0168581 A1 | 6/2018 | Hunter et al. |
| 2018/0168585 A1 | 6/2018 | Shelton, IV et al. |
| 2018/0168620 A1 | 6/2018 | Huang et al. |
| 2018/0168622 A1 | 6/2018 | Shelton, IV et al. |
| 2018/0168628 A1 | 6/2018 | Hunter et al. |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168644 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0250085 A1 | 9/2018 | Simi et al. |
| 2018/0296213 A1 | 10/2018 | Strobl |
| 2018/0310935 A1 | 11/2018 | Wixey |
| 2018/0310948 A1 | 11/2018 | Stamm et al. |
| 2018/0317915 A1 | 11/2018 | McDonald, II |
| 2019/0000454 A1 | 1/2019 | Swayze et al. |
| 2019/0000525 A1 | 1/2019 | Messerly et al. |
| 2019/0015124 A1 | 1/2019 | Williams et al. |
| 2019/0029746 A1 | 1/2019 | Dudhedia et al. |
| 2019/0059894 A1 | 2/2019 | Kumada et al. |
| 2019/0076143 A1 | 3/2019 | Smith |
| 2019/0083086 A1 | 3/2019 | Klaffenböck et al. |
| 2019/0083819 A1 | 3/2019 | Mitchell et al. |
| 2019/0099181 A1 | 4/2019 | Shelton, IV et al. |
| 2019/0125347 A1 | 5/2019 | Stokes et al. |
| 2019/0133571 A1 | 5/2019 | Racenet et al. |
| 2019/0142531 A1 | 5/2019 | Wentworth et al. |
| 2019/0167266 A1 | 6/2019 | Patel et al. |
| 2019/0192137 A1 | 6/2019 | Shelton, IV et al. |
| 2019/0201146 A1 | 7/2019 | Shelton, IV et al. |
| 2019/0231350 A1 | 8/2019 | Scott et al. |
| 2019/0239881 A1 | 8/2019 | Laurent et al. |
| 2019/0282233 A1 | 9/2019 | Burbank et al. |
| 2019/0290374 A1 | 9/2019 | Ramadorai |
| 2019/0298346 A1 | 10/2019 | Shelton, IV et al. |
| 2019/0298356 A1 | 10/2019 | Shelton, IV et al. |
| 2019/0314107 A1 | 10/2019 | Worrell et al. |
| 2019/0365458 A1 | 12/2019 | Whitlock et al. |
| 2020/0205811 A1 | 7/2020 | Posey et al. |
| 2021/0000557 A1 | 1/2021 | Mustufa et al. |
| 2021/0153927 A1 | 5/2021 | Ross et al. |
| 2021/0161529 A1 | 6/2021 | Wixey |
| 2021/0177412 A1 | 6/2021 | Wilson et al. |
| 2021/0177495 A1 | 6/2021 | Ross et al. |
| 2021/0177500 A1 | 6/2021 | Khalaji |
| 2021/0196350 A1 | 7/2021 | Fiebig et al. |
| 2021/0236119 A1 | 8/2021 | Chavan et al. |
| 2021/0267596 A1 | 9/2021 | Fanelli et al. |
| 2021/0386427 A1 | 12/2021 | Millman et al. |
| 2022/0015763 A1 | 1/2022 | Wixey et al. |
| 2022/0015823 A1 | 1/2022 | Wilson et al. |
| 2022/0031346 A1 | 2/2022 | Parks |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0125428 A1 | 4/2022 | Ragosta et al. |
| 2022/0160358 A1 | 5/2022 | Wixey |
| 2022/0167985 A1 | 6/2022 | George et al. |
| 2022/0183686 A1 | 6/2022 | Wixey et al. |
| 2022/0192665 A1 | 6/2022 | Wellman |
| 2022/0346790 A1 | 11/2022 | Wellman |
| 2022/0378537 A1 | 12/2022 | Hites et al. |
| 2022/0395270 A1 | 12/2022 | Patel et al. |
| 2023/0020577 A1 | 1/2023 | Kerver et al. |
| 2023/0047784 A1 | 2/2023 | Patel et al. |
| 2023/0052074 A1 | 2/2023 | Wixey |
| 2023/0101993 A1 | 3/2023 | Baril et al. |
| 2023/0120209 A1 | 4/2023 | Parks et al. |
| 2023/0210527 A1 | 7/2023 | Shelton, IV et al. |
| 2023/0225731 A1 | 7/2023 | Burbank |
| 2023/0329711 A1 | 10/2023 | Wixey et al. |
| 2024/0023961 A1 | 1/2024 | Wixey et al. |
| 2024/0065690 A1 | 2/2024 | Jasemian et al. |
| 2024/0081824 A1 | 3/2024 | Hites |
| 2024/0108343 A1 | 4/2024 | Wixey |
| 2024/0138834 A1 | 5/2024 | Wellman |
| 2024/0252171 A1 | 8/2024 | Wixey et al. |
| 2024/0260959 A1 | 8/2024 | Wixey et al. |
| 2024/0293122 A1 | 9/2024 | Wixey |
| 2024/0315761 A1 | 9/2024 | Whitlock et al. |
| 2024/0335194 A1 | 10/2024 | Patel et al. |
| 2024/0341766 A1 | 10/2024 | Millman et al. |
| 2024/0407782 A1 | 12/2024 | Patel et al. |

FOREIGN PATENT DOCUMENTS

| | | |
|---|---|---|
| CN | 105007836 A | 10/2015 |
| CN | 105769331 A | 7/2016 |
| CN | 106232026 A | 12/2016 |
| CN | 106491203 A | 3/2017 |
| CN | 107920819 A | 4/2018 |
| CN | 108024809 A | 5/2018 |
| CN | 112165909 A | 1/2021 |
| DE | 694747 C | 8/1940 |
| DE | 3724525 C1 | 5/1988 |
| DE | 102012103503 A1 | 10/2013 |
| EP | 0277532 B1 | 8/1990 |
| EP | 0469396 A1 | 2/1992 |
| EP | 0277529 B1 | 4/1993 |
| EP | 0641546 A1 | 3/1995 |
| EP | 0986336 A1 | 3/2000 |
| EP | 1090592 A1 | 4/2001 |
| EP | 1479348 A1 | 11/2004 |
| EP | 1728473 A1 | 12/2006 |
| EP | 1479346-81 | 1/2007 |
| EP | 1621141 B1 | 7/2007 |
| EP | 2374419 A2 | 10/2011 |
| EP | 1316290-81 | 2/2012 |
| EP | 2517639 A1 | 10/2012 |
| EP | 2540231 A2 | 1/2013 |
| EP | 1754445 B1 | 10/2013 |
| EP | 2777529 A1 | 9/2014 |
| EP | 2777530 A1 | 9/2014 |
| EP | 2777532 A2 | 9/2014 |
| EP | 2779921 A2 | 9/2014 |

(56) References Cited

FOREIGN PATENT DOCUMENTS

| | | | |
|---|---|---|---|
| EP | 2944275 | A2 | 11/2015 |
| EP | 2992834 | A1 | 3/2016 |
| EP | 2992849 | A1 | 3/2016 |
| EP | 3000408 | A2 | 3/2016 |
| EP | 3120780 | A2 | 1/2017 |
| EP | 3135225 | A2 | 3/2017 |
| EP | 3158947 | A1 | 4/2017 |
| EP | 3173029 | A1 | 5/2017 |
| EP | 3205291 | A1 | 8/2017 |
| EP | 3338703 | A1 | 6/2018 |
| FR | 2828952 | B1 | 12/2005 |
| JP | S5794132 | A | 6/1982 |
| JP | 2001170069 | A | 6/2001 |
| JP | 5301166 | B2 | 9/2013 |
| JP | 2014530653 | A | 11/2014 |
| JP | 2016508792 | A | 3/2016 |
| JP | 2016513570 | A | 5/2016 |
| JP | 2017500146 | A | 1/2017 |
| JP | 2017513564 | A | 6/2017 |
| JP | 2017527396 | A | 9/2017 |
| JP | 6411461 | B2 | 10/2018 |
| JP | 2019141659 | A | 8/2019 |
| SU | 405234 | A1 | 9/1975 |
| SU | 886900 | A1 | 12/1981 |
| SU | 1333319 | A2 | 8/1987 |
| SU | 1442191 | A1 | 12/1988 |
| SU | 1459659 | A1 | 2/1989 |
| WO | WO-8602254 | A1 | 4/1986 |
| WO | WO-9005489 | A1 | 5/1990 |
| WO | WO-9734533 | A1 | 9/1997 |
| WO | WO-03094743 | A1 | 11/2003 |
| WO | WO-03094746 | A1 | 11/2003 |
| WO | WO-03094747 | A1 | 11/2003 |
| WO | WO-2004020859 | A1 | 3/2004 |
| WO | WO-2009112802 | A1 | 9/2009 |
| WO | WO-2012142872 | A1 | 10/2012 |
| WO | WO-2014106275 | A1 | 7/2014 |
| WO | WO-2016073538 | A1 | 5/2016 |
| WO | WO-2017026141 | A1 | 2/2017 |
| WO | WO-2017034803 | A2 | 3/2017 |
| WO | WO-2017156070 | A1 | 9/2017 |
| WO | WO-2017214243 | A1 | 12/2017 |
| WO | WO-2018005750 | A1 | 1/2018 |
| WO | WO-2018071497 | A1 | 4/2018 |
| WO | WO-2018118402 | A1 | 6/2018 |
| WO | WO-2019090047 | A1 | 5/2019 |
| WO | WO-2020081960 | A1 | 4/2020 |
| WO | WO-2020131685 | A1 | 6/2020 |
| WO | WO-2020131692 | A1 | 6/2020 |
| WO | WO-2022150215 | A1 | 7/2022 |

OTHER PUBLICATIONS

Extended European Search Report for Application No. EP19757451.0, mailed on May 19, 2022, 16 pages.
Extended European Search Report for Application No. EP19898247.2, mailed on Jan. 10, 2023, 12 pages.
Extended European Search Report for Application No. EP19900059.7, mailed on Dec. 5, 2022, 10 pages.
Extended European Search Report for Application No. EP20790773.4, mailed on Nov. 29, 2022, 09 pages.
Extended European Search Report for Application No. EP20815112.6, mailed on Jan. 5, 2023, 11 pages.
Extended European Search Report for Application No. EP20875978.7, mailed on Jan. 31, 2024, 26 pages.
Extended European Search Report for Application No. EP24155564.8, mailed on Jul. 8, 2024, 12 pages.
European Search Report (Corrected version) for Application No. EP19750317.0, mailed on Mar. 28, 2022, 26 pages.
International Search Report and Written Opinion for Application No. PCT/US2020/054568. mailed Jan. 29, 2021, 13 pages.
International Preliminary Report on Patentability for Application No. PCT/US2019/017646, mailed on Aug. 27, 2020, 10 pages.
International Preliminary Report on Patentability for Application No. PCT/US2019/019501, mailed Sep. 3, 2020, 7 pages.
International Search Report and Written Opinion for Application No. PCT/US2020/025655, mailed Jul. 22, 2020, 8 pages.
International Search Report and Written Opinion for Application No. PCT/US19/17646, mailed on Apr. 16, 2019, 11 pages.
International Search Report and Written Opinion for Application No. PCT/US2019/019501. mailed May 9, 2019, 8 pages.
International Search Report and Written Opinion for Application No. PCT/US2019/056979, mailed Dec. 18, 2019, 8 pages.
International Search Report and Written Opinion for Application No. PCT/US2019/062344, mailed Mar. 23, 2020, 17 pages.
International Search Report and Written Opinion for Application No. PCT/US2019/062768, mailed Mar. 9, 2020, 15 pages.
International Search Report and Written Opinion for Application No. PCT/US2019/064861, mailed Mar. 30, 2020, 18 pages.
International Search Report and Written Opinion for Application No. PCT/US2019/066513, mailed Apr. 21, 2020, 8 pages.
International Search Report and Written Opinion for Application No. PCT/US2019/066530, mailed Apr. 21, 2020, 8 pages.
International Search Report and Written Opinion for Application No. PCT/US202 1/065544 mailed Jun. 2, 2022, 21 pages.
International Search Report and Written Opinion for Application No. PCT/US2020/020672, mailed Jun. 29, 2020, 10 pages.
International Search Report and Written Opinion for Application No. PCT/US2020/033481, mailed Sep. 3, 2020, 22 pages.
International Search Report and Written Opinion for Application No. PCT/US2021/012284 mailed May 6, 2021, 23 pages.
Partial European Search Report for Application No. EP19757451.0, mailed on Feb. 2, 2022, 12 pages.
Supplementary European Search Report for Application No. EP19873128.3, mailed on Jun. 22, 2022, 7 pages.
International Search Report and Written Opinion for Application No. PCT/US2021/065308, mailed Apr. 21, 2022, 13 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Field Application Note—Journal Bearings, Retrieved from Wayback Machine URL: https://web.archive.org/web/20100110095051/http://www.reliabilitydirect.com/appnotes/jb.html, on Mar. 12, 2024, 04 pages.
International Search Report and Written Opinion for Application No. PCT/US2016/059527, mailed on Feb. 16, 2017, 13 pages.
Nicholson, C., et al., "Plane Bearings," ESC Report, BSA Educational Services Committee, Oct. 1994, vol. 5(1), 02 pages.
Burstein M.D., "8 MM Sureform 30 Staplers and Reloads," Sages, Jun. 2022, 1 Page. Retrieved from internet URL: https://www.accessdata.fda.gov/cdrh_docs/pdf21/K211997.pdf.
Extended European Search Report for Application No. EP18823002.3 mailed on Mar. 5, 2021,11 pages.
International Search Report and Written Opinion for Application No. PCT/US2018/039912, mailed on Oct. 12, 2018, 15 pages.
Jaggi A., "8 mm SureForm 30 Curved-Tip Stapler, 8 mm SureForm 30 Stapler, SureForm 30 Reloads," U.S Food & Drug Administration, Dec. 2021. 11 pages. Retrieved from the internet URL:https://www.sages.org/publications/tavac/8-mm-sureform-30-staplers-and-reloads/.

* cited by examiner

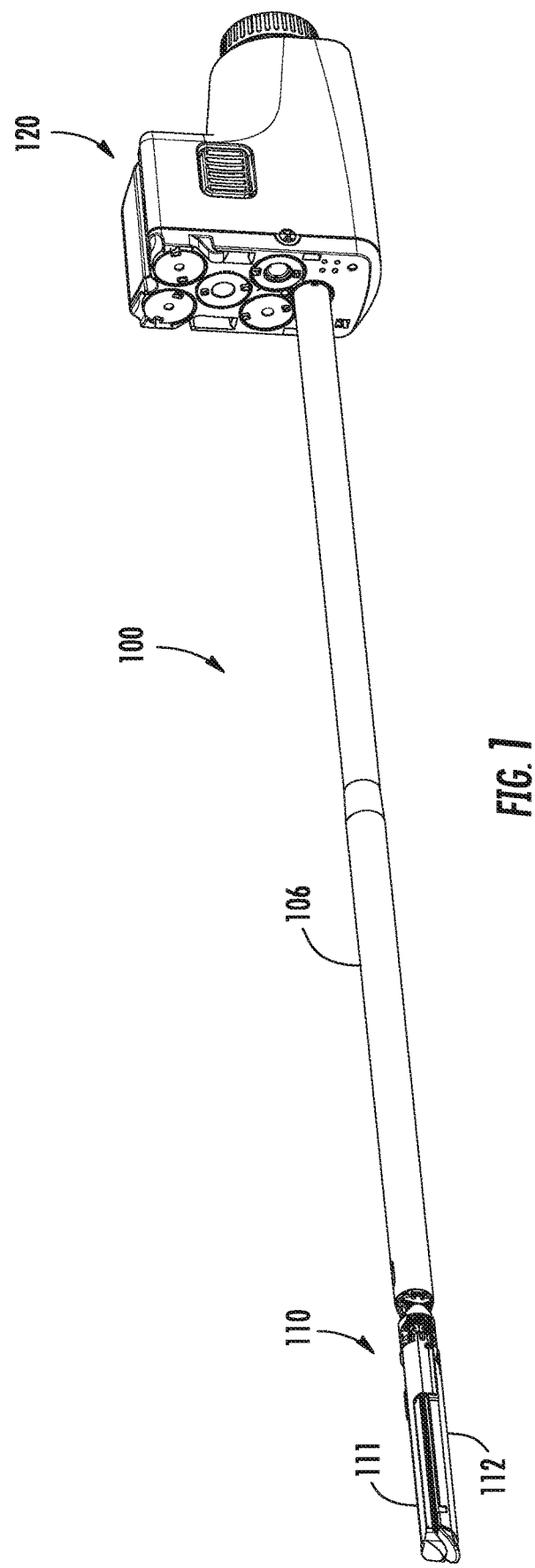

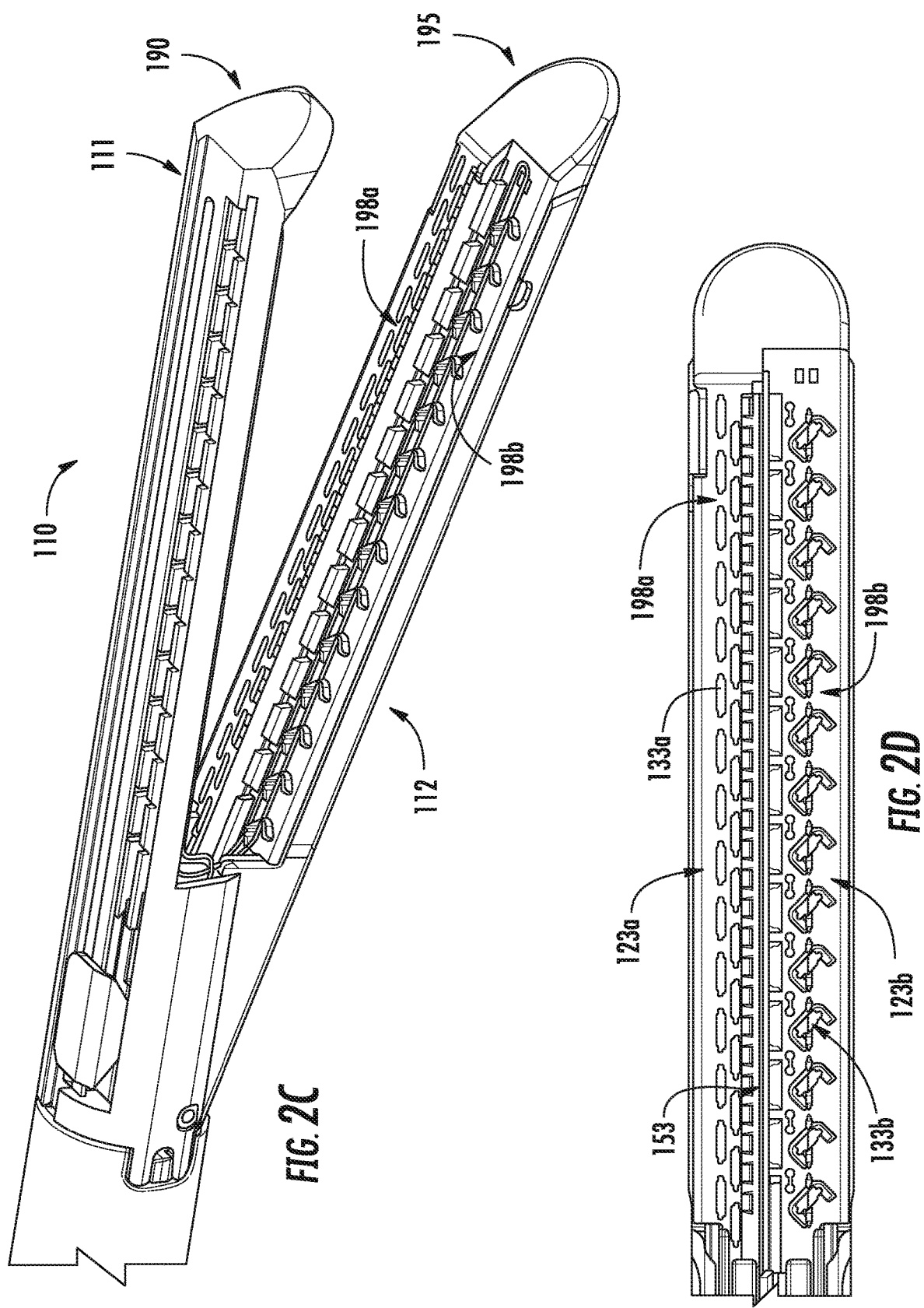

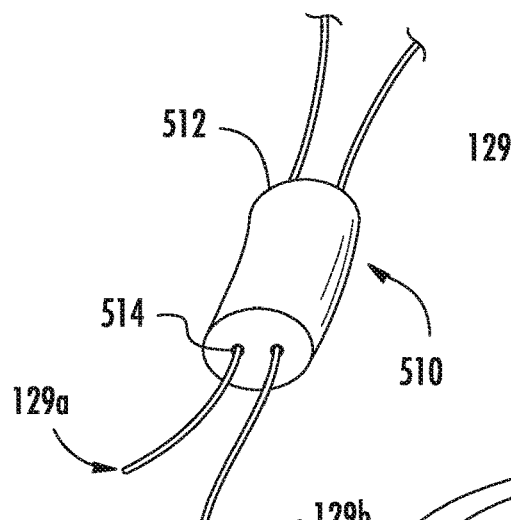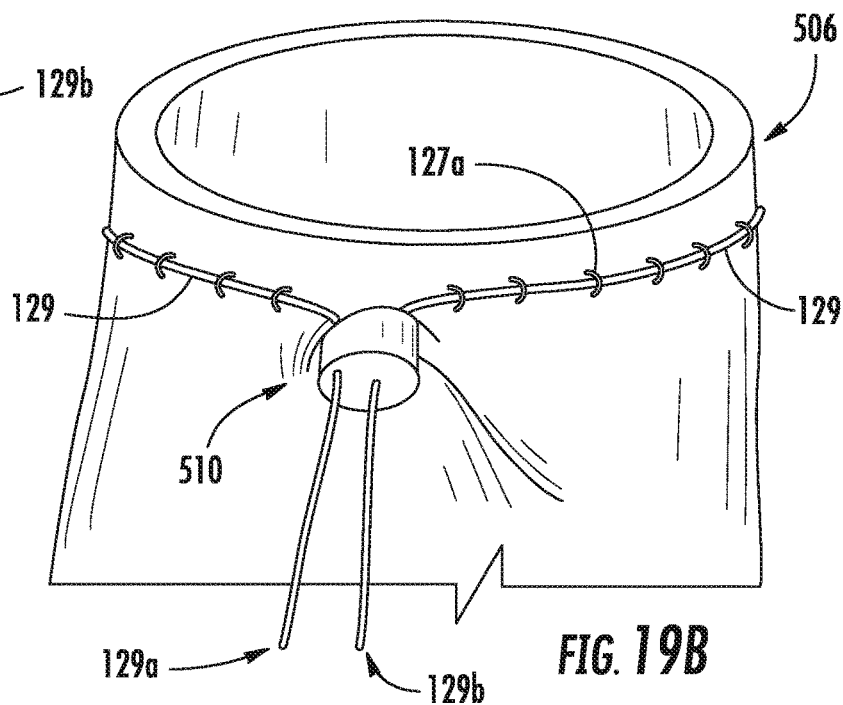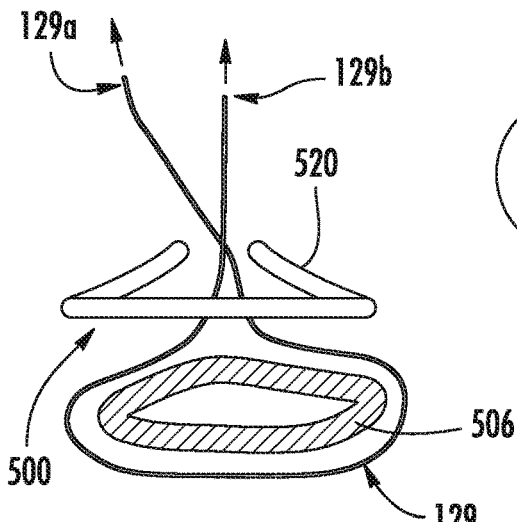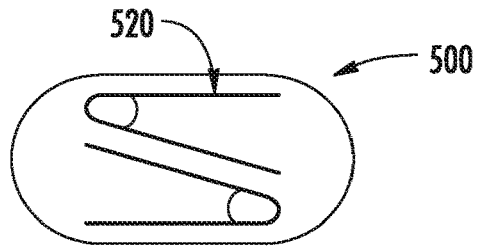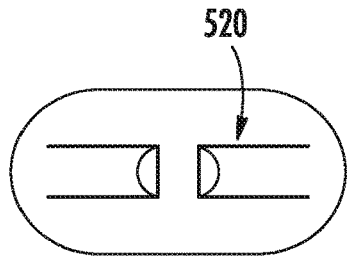
FIG. 19A
FIG. 19B
FIG. 20A
FIG. 20B
FIG. 20C

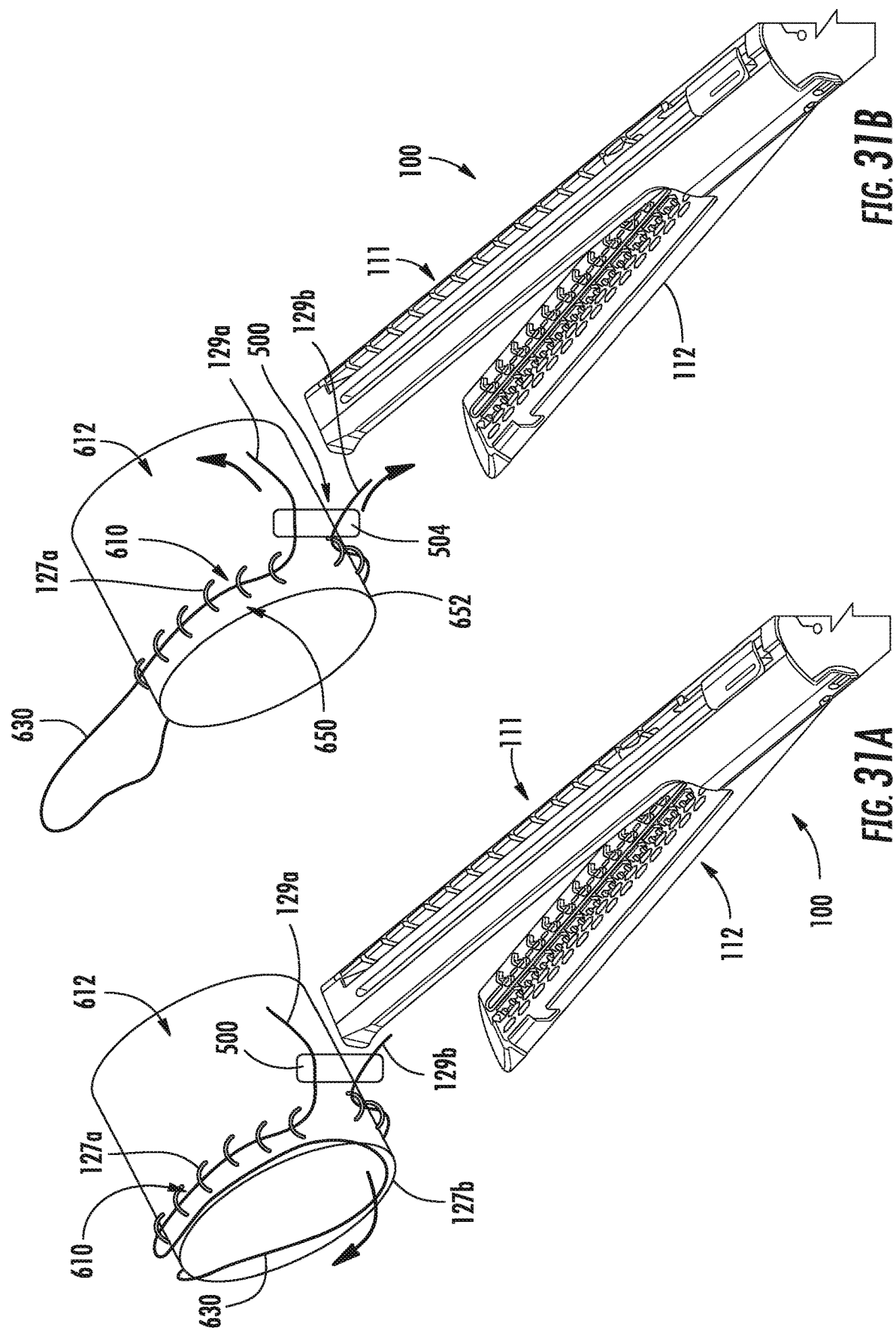

SURGICAL INSTRUMENT WITH LINEAR AND PURSE STRING SUTURE STAPLES

CROSS REFERENCE TO RELATED APPLICATIONS

This application is the National Stage of International Application No. PCT/US21/65308, filed on Dec. 28, 2021, which claims benefit of U.S. Provisional Application No. 63/134,961, filed Jan. 8, 2021, the entire disclosure of which is incorporated herein by reference for all purposes.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI™ system commercialized by Intuitive Surgical, Inc. of Sunnyvale, California.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. No. 7,594,912 (filed Sep. 30, 2004), U.S. Pat. No. 6,758,843 (filed Apr. 26, 2002), U.S. Pat. No. 6,246,200 (filed Aug. 3, 1999), and U.S. Pat. No. 5,800,423 (filed Jul. 20, 1995), the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. No. 6,702,805 (filed Nov. 9, 2000), U.S. Pat. No. 6,676,669 (filed Jan. 16, 2002), U.S. Pat. No. 5,855,583 (filed Nov. 22, 1996), U.S. Pat. No. 5,808,665 (filed Sep. 9, 1996), U.S. Pat. No. 5,445,166 (filed Apr. 6, 1994), and U.S. Pat. No. 5,184,601 (filed Aug. 5, 1991), the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical anastomosis joins together two hollow organs, usually to restore continuity after resection, or less commonly to bypass an unresectable disease process. For example, during a lower anterior resection (LAR) procedure, a portion of the intestines near the rectum is removed. The surgeon typically applies a linear staple line across the bowel to seal the healthy portion of the bowel and to resect the tissue to be removed, leaving at least one linear staple line on the distal stump of the rectum. During the anastomosis, a circular stapler is advanced through the bowel and the two remaining ends of the bowel are drawn together so that they can be joined in an anastomosis with the circular stapler.

Unfortunately, there are often complications with this procedure because the linear staple line interacts with the circular stapler when the circular staple line crosses over the linear staple line to form the anastomosis. To resolve this problem, a purse string suture can be applied to the bowel to cinch the bowel and prevent or eliminate the linear and circular staple lines from crossing. The purse string suture is typically placed using a needle, staples or other suitable means for attaching the suture to the tissue. After attachment, the ends of the suture remain loose for pulling to contract or cinch close the bowel tissue.

One of the drawbacks with this procedure is that the purse-string suture is difficult to perform manually (i.e., hand-sewn) in a closed abdomen procedure. In addition, the purse string hoop is typically held down via a series of knots, which makes the purse string hoop non-compliant. If the purse string hoop is too tight, it will rupture when the either the spike or the anvil posts of the circular stapler enter the purse string hoop.

Another drawback with existing devices and procedures is that the distance between the linear stapler line and the transection plane (i.e., the line of dissection of the bowel) is limited by the geometry of the stapler device. In order to provide a successful interaction between the purse string suture and the circular stapler, a sufficient amount of tissue must be preserved between the purse string staples and the transection plane. This is known as a "tissue cuff". Tissue cuff provides compliance within the purse string hoop. The more "tissue cuff" that can be achieved, the less likely there will be complications with the circular stapler. Tissue within the purse string hook makes it less likely that an interaction will occur. In addition, it provides confidence to the user that tissue will completely cover the staple zone of the circular stapler.

In minimally invasive surgical anastomosis procedures, it would be advantageous to provide surgical instruments and devices that enable faster, easier and more consistent purse string suture hoops to be applied to tissue, such as bowel tissue. In addition, it would be desirable to increase the tissue cuff between the purse string suture hoop and the transection plane to facilitate the user drawing the purse string hoop closed and to minimize complications with the circular stapler performing the anastomosis.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

In one aspect, a surgical stapling instrument comprises an elongate shaft and an end effector coupled to the distal end of the shaft and comprising first and second jaws configured to move between open and closed positions. The instrument includes a first row of staples in each of the first and second jaws having a suture extending therethrough and a second row of staples in the second jaw on an opposite side of the longitudinal axis from the first row of staples. A drive member is configured to translate distally through the end effector to drive the first and second row of staples into tissue such that the suture is disposed between the first row of staples and the tissue. The instrument may further include a cutting element coupled to the drive member and configured to dissect tissue as the drive member translates distally through the first and second jaws.

The drive member is preferably configured to drive the first row of staples into tissue such that the suture, in combination with the staples, forms a purse string with the tissue. This is achieved by securing a suture to the outer surface of the tissue via staples that pinch the surface of the tissue.

Accordingly, surgical instruments disclosed herein can simultaneously transect tissue, apply a linear staple line along one side of the tissue dissection and apply a suture, such as a purse string suture, to the other side of the tissue dissection. These instruments are particularly useful for dissection of bowl tissue. For example, the tissue dissection allows for the two ends of the bowel to be separated for eventual removal of the resected specimen. The application of the linear staple line allows the user to close one end of the specimen to prevent content spillage. The application of a purse-string suture on the other end allows the user to cinch the bowel and prepare it for eventual anastomosis after the unwanted tissue has been removed. Performing all three of these functions with a single instrument makes the entire procedure faster, easier and more consistent for the user. In addition, it minimizes complications associated with crossing staple lines when used with an end-to-end circular stapler (e.g., during bowel resection procedures).

In certain embodiments, the distance between the purse string staples and the cutting element along the tissue contacting surfaces of the jaws is greater than a distance between the linear staples and the cutting element. This increases the amount of "tissue cuff" between the resection line and the purse string staples, thereby minimizing complications between the purse string staples and the circular stapler during the anastomosis.

In one such embodiment, the cutting element is disposed laterally from the longitudinal axis on an opposite side from the purse string suture staples. Thus, the distance between the cutting element and the purse string staples is increased, thereby increasing the size of the tissue cuff.

In another embodiment, the purse string staples in the first and second jaws are oriented at a transverse angle relative to the longitudinal axis of the shaft such that one of the staple legs of each staple is distal to the other staple leg. This configuration angles the purse string staples away from the transection line, thereby increasing the size of the tissue cuff.

In yet another embodiment, the first and second jaws each comprise an angled portion on their tissue contacting surfaces that extends downwardly from a first axis to a second axis. The first axis is closer to the upper portion of the shaft than the second axis. The angled portion of the tissue contacting surfaces extends downwardly from the cutting element towards the purse string staples. This creates a jog in the plane in which the tissue sits between the jaws of the device, thereby increasing the length of the tissue contacting surfaces between the cutting element and the purse string staples.

The surgical instruments may include one of the above embodiments, all of them, or any combination of them.

The first row of staples in the first jaw may be offset longitudinally from the first row of staples in the second jaw such that each staple in the first jaw is disposed between two staples in the second jaw in the longitudinal direction (and vice versa). This allows the staples in the first jaw to be positioned closer to the staples in the second jaw in the pre-fired position (i.e., before the staples are driven into tissue). Offsetting the staples in this manner provides more space in the jaws, thereby providing a more compact and maneuverable instrument.

The instrument may further comprise a cartridge removably coupled to the first and second jaws. The cartridge includes a shuttle configured to engage the first row of staples in the second jaw and the second row of staples as the drive member is translated distally through the first and second jaws. The shuttle engages the staples and drives them into tissue. The drive member may comprise a distal portion configured to engage the first row of staples in the first jaw as the drive member is translated distally through the first and second jaws. This distal portion may be integral with the drive member and is configured to drive the staples into tissue.

The drive member may comprise a main body and a lateral portion extending laterally outward from the main body. The lateral portion includes one or more distal inclined ramps configured for engaging the staples in the first jaw to drive them into tissue. The lateral portion may be integral with the drive member, which eliminates the requirement for a separate shuttle in the staple cartridge for actuating the row of staples in the first jaw. This creates more space in the suture cartridge, thereby allowing for the design of a more compact and maneuverable instrument.

The instrument may further comprise an actuation mechanism configured to translate the drive member distally through the end effector. The actuation mechanism may be coupled to a control device of a robotic telesurgical system that may, for example, allow for mechanical actuation and control of the surgical instrument to perform a variety of functions, such as closing the jaws, dissecting and stapling tissue, or the like, in response to manipulation of master input devices located remotely from the surgical instrument.

In another aspect, a surgical stapling instrument comprises an elongate shaft and an end effector coupled to the distal end of the shaft having first and second jaws configured to move between open and closed positions. The instrument includes a first row of staples in each of the first and second jaws with a suture extending therethrough. A suture holding member is disposed within the end effector such that at least one of the free ends of the suture is coupled to the suture holding member. A drive member is configured to translate distally through the first and second jaws to drive the first and second rows of staples into tissue such that the suture extends between the staples and the tissue.

The suture holding member allows the user to apply a purse string hoop around tissue without having to tie knots to hold the purse string hoop tight, thereby making the procedure easier, faster and more consistent than conventional procedures. In addition, the suture holding member provides some degree of compliance to the purse string hoop, such that the purse string has some "give" when the circular stapler spike and/or anvil post enters the purse string hoop. This minimizes or eliminates rupture of the purse string suture when the circular stapler is performing the anastomosis. In addition, the suture holding member allows the operator to loosen the purse string hoop, if desired.

In certain embodiments, the suture holding member may be configured such that both the first and second free ends of the suture extend therethrough. This allows the user to easily tighten down the purse string hoop simply by holding the suture holding member and pulling the frees ends of the suture.

In one such embodiment, the suture holding member comprises a tissue contacting surface and the suture extends through the suture holding member such that the first and second free ends extend substantially tangential to the tissue contacting surface. Thus, the suture extends through the suture holding member such that the first and second free ends extend away from the suture holding member in substantial opposite directions from each other. This minimizes the tension on the adjacent staples as the suture is tightened, i.e., the holding member acts as a passive pulley that absorbs at least some of force applied by the sutures as they are pulled and tightened.

In another such embodiment, the suture holding member comprises a tissue contacting surface and the suture extends through the suture holding member such that the first and second free ends extend substantially radially to the tissue contacting surface. Thus, the suture extends through the suture holding member such that the first and second free ends extend away from the suture holding member in substantial the same direction. This allows the user to tighten the purse string suture via a surgical "draw down" technique in which one hand holds the suture holding member down, while the other hand pulls both suture ends away from the holding member.

The suture holding member may have a tissue contacting surface, and a second surface opposite the tissue contacting surface. The suture holding member is disposed within the end effector such that the second surface faces a distal end of the end effector when the staples have been driven into the tissue. In this manner, the suture holding member will be facing the same direction that the instrument approached the tissue after the purse string hoop has been applied to the bowel. This improves visualization of the suture holding member and positions the suture holding member closer to the user, thereby allowing the user to immediately visualize the suture holding member after the purse string hoop has been applied to the tissue. This makes it easier to tighten down the suture holding member (e.g., without having to search for the suture holding member on the other side of the bowel).

The first and second jaws may each comprise a longitudinal channel for receiving a portion of the suture that is substantially parallel with the row of staples. The suture holding member is disposed proximal to the row of staples. The suture extends from the suture holding member distally through the row of staples in the first jaw, proximally through the channel in the first jaw, distally through the channel in the second jaw and then proximally through the row of staples in the second jaw such that the second free end is disposed proximally of the first row of staples. Thus, the suture forms a substantially U-shape in each of the first and second jaws, thereby allowing a user to apply the suture and suture holding member to tissue with the instrument such that the suture holding member is facing the instrument.

The suture may be coupled to the suture holding member and configured to release under a threshold level of tension. This allows the suture holding member to hold the suture when tightened down and generally manipulated, but would release under some level of tension. For example, as the circular stapler enters the purse string hoop and stretches it wider, the suture holding member will release if the tension level becomes sufficiently high to rupture the purse string hoop.

The suture holding member may comprise a compliant material, such as rubber or a similarly compliant material. The suture holding member may be designed with compliant features to allow such functionality. The suture may be woven through the suture holding member to create a friction fit between the suture and the holding member. This friction fit is strong enough to hold the suture holding member down against the tissue, but compliant enough to minimize or avoid rupture of the purse string hoop during the anastomosis.

The suture holding member may include one or more locking elements that provide a non-linear path for the suture either through the suture holding member, or as the suture exits the holding member. The locking elements are configured to hold the suture under a certain level of tension, while providing sufficient compliance to prevent rupture of the purse string hoop during the anastomosis.

The first and second ends of the suture may extend through openings in the suture holding member. The suture holding member is configured to hold the suture with friction, while allowing the suture to have some degree of movement relative to the suture holding member at a threshold force. In an exemplary embodiment, the suture has a length selected to allow the bowel to expand to its natural, unconstrained configuration with the free ends of the suture extending through the suture holding member. In one such embodiment, the free ends of the suture are coupled to each other (or designed as a loop such that there is no "free end") to ensure that the suture does not withdraw through the suture holding member. This allows the bowel to expand while ensuring that the suture will remain in position around the bowel and secure within the suture holding member.

In another embodiment, a first free end of the suture is coupled to the suture holding member, and the suture holding member comprises an opening for receiving the second free end of the suture. The opening includes an enlarged region for passing the second free end of the suture therethrough, and a narrowed slot for securing the second free end of the suture to the suture holding member. This allows the user to feed the second free end of the suture into the opening, cinch the purse string hoop tight, and then draw the suture into the narrowed slot to secure the suture and keep the purse string hoop tight throughout the remainder of the procedure. In other embodiments, the suture holding member and/or the suture includes one or more features (e.g., directional barbs on the suture, zip ties, crimps or other locking elements on the suture holding member) that allow the suture to be easily fed or pulled therethrough in one direction, while resisting movement in the opposite direction.

It is to be understood that both the foregoing general description and the following detailed description are exemplary and explanatory only and are not restrictive of the disclosure. Additional features of the disclosure will be set forth in part in the description which follows or may be learned by practice of the disclosure

BRIEF DESCRIPTION OF THE DRAWINGS

The above and other aspects, features, and advantages of the present surgical instruments will become more apparent in light of the following detailed description when taken in conjunction with the accompanying drawings in which:

FIG. 1 is a perspective view of an illustrative surgical instrument;

FIG. 2C is a perspective view of the end effector of FIG. 1 with the jaws in the angled open position;

FIG. 2D is a top-down view of one of the jaws of the end effector of FIG. 1;

FIG. 19A illustrates another embodiment of a suture holding member;

FIG. 19B illustrates the suture holding member of FIG. 19A being used to cinch representative tissue;

FIGS. 20A-20C illustrate other embodiments of a suture holding member with a locking element;

FIGS. 31A and 31B schematically illustrate a surgical instrument placing a purse string suture hoop onto tissue.

DETAILED DESCRIPTION

Figure 2A:
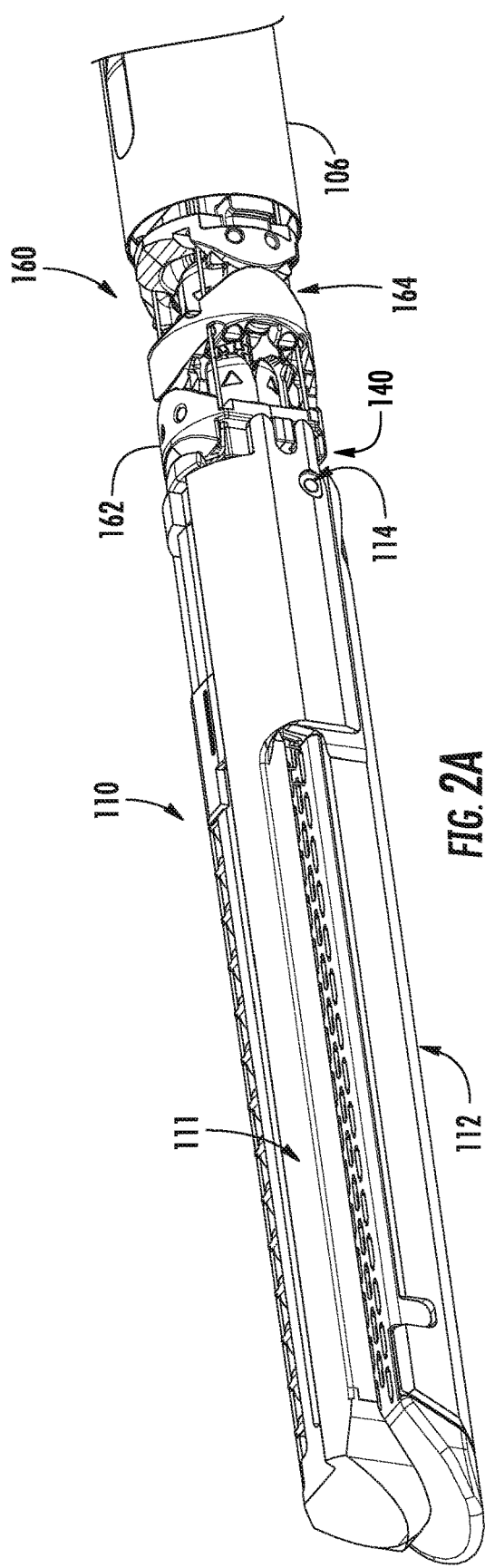
FIG. 2A is a side view of the distal end portion of the surgical instrument of FIG. 1 having an end effector mounted to an elongated shaft.

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

While the following is presented with respect to a surgical instrument for forming purse strings and linear staples, it should be understood that certain features of the presently described surgical instruments may be readily adapted for use in any type of surgical clamping, cutting, or sealing instruments. In addition the surgical clamping and cutting instrument may be a minimally invasive (e.g., laparoscopic) instrument or an instrument used for open surgery.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

FIG. 1 is a perspective view of an illustrative surgical instrument 100 having a backend mechanism 120, and an end effector 110 with first and second jaws 111, 112 mounted on an elongated shaft 106. Backend mechanism 120 typically provides a mechanical coupling between the drive tendons or cables of the instrument and motorized axes of the mechanical interface of a drive system. Further details of known backend mechanisms and surgical systems are described, for example, in U.S. Pat. Nos. 8,597,280, 7,048,745, and 10,016,244. Each of these patents is hereby incorporated by reference in its entirety.

Actuation mechanisms of surgical instrument 100 employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties.

Figure 2B:
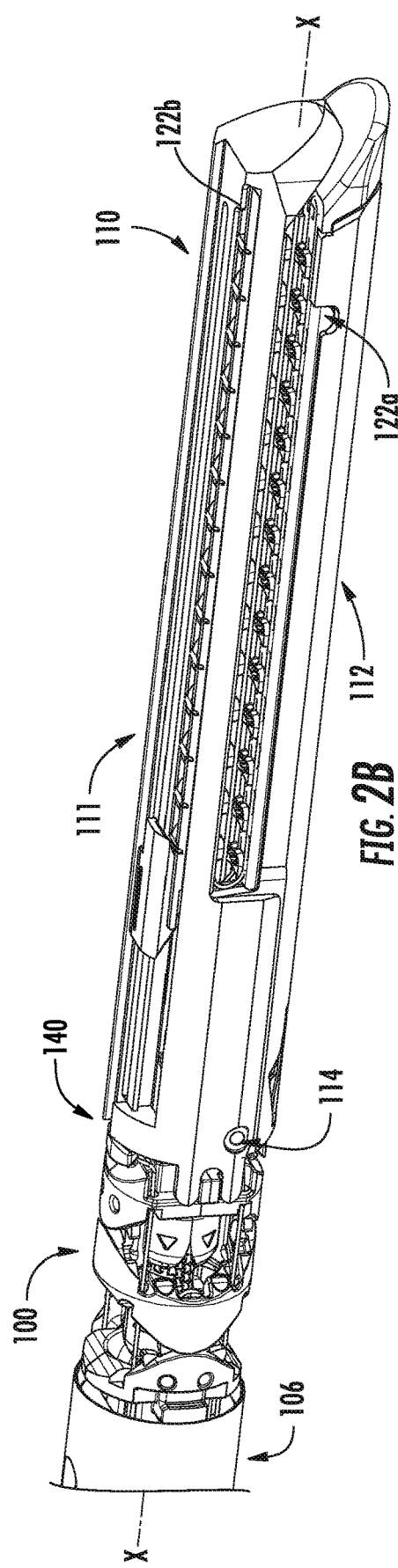
FIG. 2B illustrates the other side of the end effector of FIG. 1 with the jaws in a substantially closed position.

FIGS. 2A-2E illustrate the distal end portion of surgical instrument 100, including an end effector 110 defining a longitudinal axis X-X and having a first jaw 111, a second jaw 112, a lower cartridge 122a, an upper cartridge 122b, a clevis 140 for mounting jaws 111, 112 to the instrument, and an articulation mechanism, such as wrist 160. First and second jaws 111, 112 are configured to move from an open position (FIGS. 2C and 2E) to a closed position (FIGS. 2A and 2B). In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other. In the open position, fresh stapling cartridges 122a, 122b (sometimes referred to as reloads and shown more clearly in FIG. 3) can be loaded into jaws 111, 112 and tissue may be positioned between the jaws 111, 112. In the closed position, jaws 111, 112 cooperate to clamp, sever and staple tissue, as discussed in more detail below.

Figure 15:
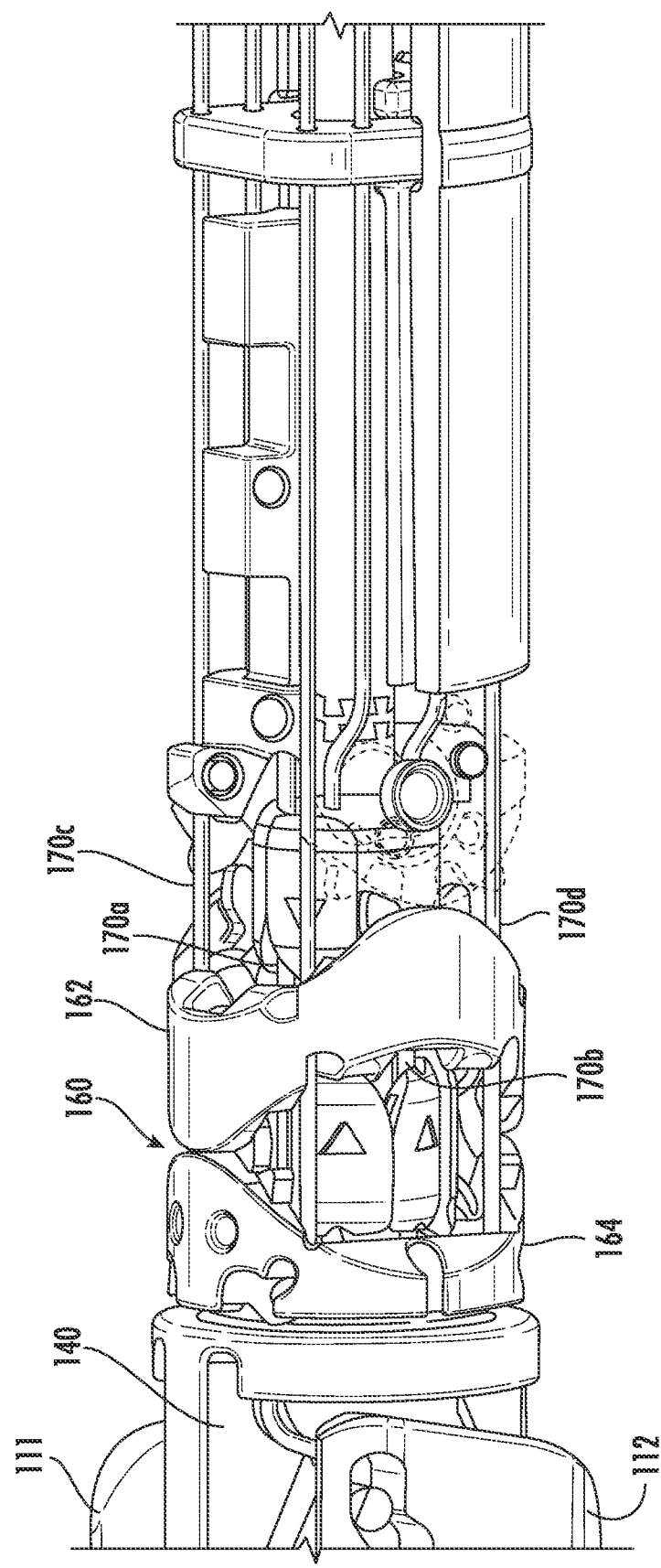
FIG. 15 is a perspective view of the articulation mechanism of the surgical instrument of FIG. 1 with parts removed to reveal internal structures.

In certain embodiments, jaws 111, 112 are attached to surgical instrument 100 via a suitable coupling device, such as a clevis 140 (see also FIG. 15). Clevis 140 includes an opening for receiving a pivot pin 114 defining a pivot axis around which jaw 112 pivots. A more complete description of a suitable clevis 140 for use with the devices disclosed herein may be found in commonly-assigned, provisional patent application Nos.: 62/783,444, filed Dec. 21, 2018; 62/783,481, filed Dec. 21, 2018; 62/783,460, filed Dec. 21, 2018; 62/747,912, filed Oct. 19, 2018; and 62/783,429, filed Dec. 21, 2018, the complete disclosures of which are hereby incorporated by reference in their entirety for all purposes. Of course, it will be recognized by those skilled in the art that other coupling mechanisms known by those skilled in the art may be used to attach the jaws 111, 112 to shaft 106 of surgical instrument 100.

Figure 3:
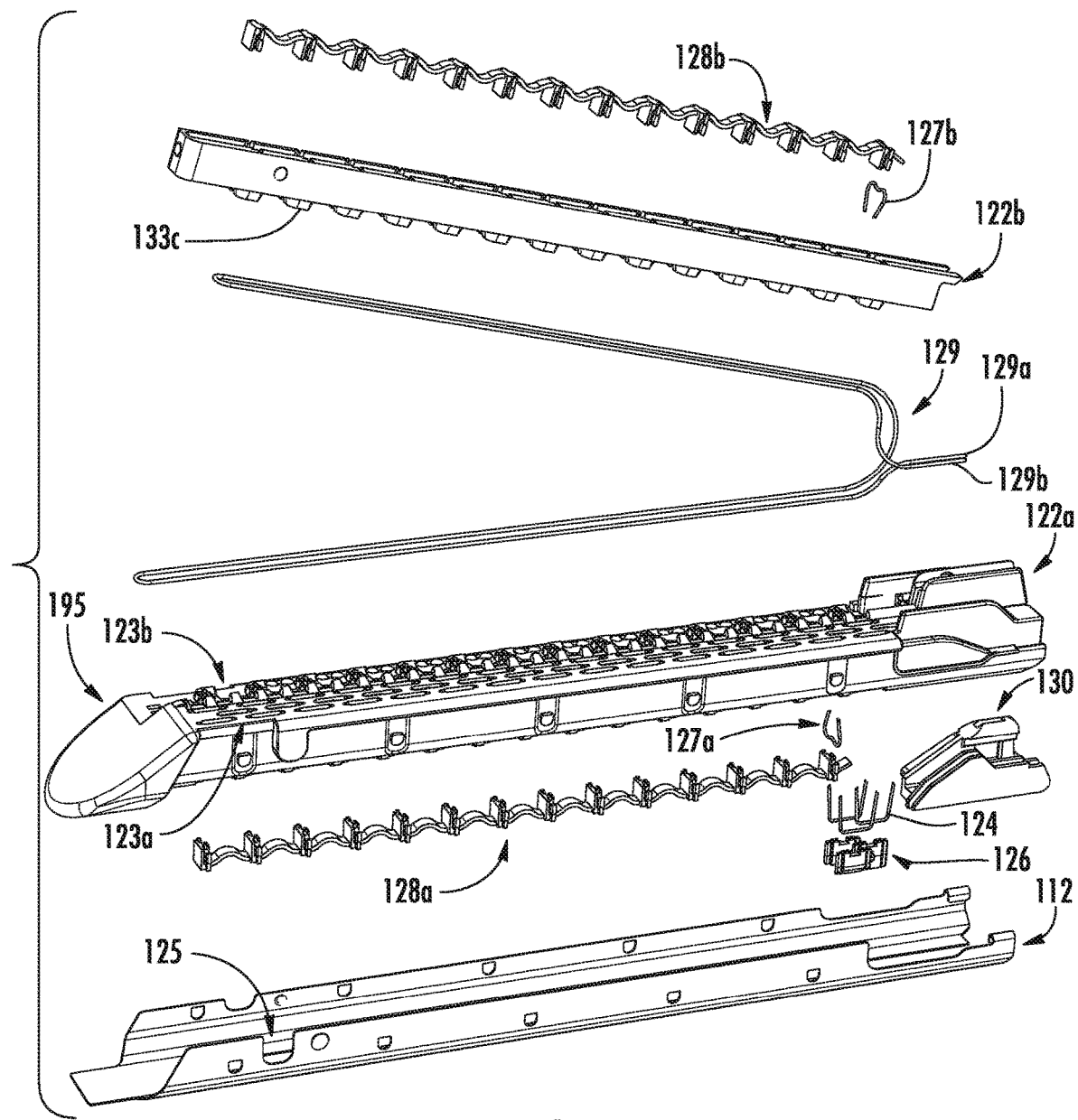
FIG. 3 is an exploded view of staple cartridges for use with the surgical instrument of FIG. 1.

Referring now to FIGS. 2D and 3, lower cartridge 122a includes an elongate body designed to fit within a cavity 125 of lower jaw 112 such that lower cartridge 122a is removably coupled to jaw 112. Alternatively, the entire lower jaw 112 may comprise the cartridge and cartridge 122a will be removably attached to a proximal portion of end effector 110. Lower cartridge 122a includes first and second sides 123a, 123b at least partially separated by a center knife channel 153 (see FIG. 7). Side 123a defines a tissue contacting surface 198a and includes staple retaining pockets 133a and side 123b defines a tissue contacting surface 198b and includes staple retaining pockets 133b. Side 123b further includes suture retaining channels (not shown) formed therein for retaining a suture 129. In certain embodiments, tissue contacting surfaces 198a, 198b may further include protrusions (not shown) positioned about staple receiving pockets 133a, 133b. Protrusions help to further secure clamped tissue and to resist movement that might be induced from forces created by the severing and stapling of clamped tissue.

Side 123a of lower cartridge 122a further includes a plurality of staple assemblies, each comprising one or more staples 124 supported on corresponding staple drivers or pushers 126 provided within staple receiving pockets 133a. Staple receiving pockets 133a may be cutouts that are substantially parallel to the longitudinal axis X-X of end effector 110, and similar in length to the desired size of staples 124 to be fired.

The staple assemblies may be designed to have one row of staples 124, two rows of staples 124 oriented parallel to each other along the longitudinal axis of end effector 110, or three or more rows of staples 124. In an exemplary embodiment, each staple assembly includes three staples oriented to form two linear rows of staples extending along side 123a of lower cartridge 122a. The term "linear staple" generally means that the staples extend substantially parallel to the longitudinal axis X-X of the end effector such that a linear staple line is applied to the tissue along this axis. The staple assemblies are preferably arranged within the compartments such that staple pushers 126 are situated near a bottom surface of lower cartridge 122a and staples 124 have their legs facing a top surface of cartridge 122a. For ease of reference, the top surface of cartridge 122a faces jaw 111 (see FIG. 2B).

Side 123b of lower cartridge 122a includes a row of staples 127a supported on corresponding staple drivers or pushers 128a provided within staple receiving pockets 133b. Staple receiving pockets 133b may be cutouts that are disposed at a partially or completely transverse angle to the longitudinal axis of end effector 110, and similar in length to the desired size of staples 127a to be fired. Side 123b of lower cartridge 122a further includes suture retaining channels 159a, 159b that extend substantially parallel to the longitudinal axis of end effector 110 (see FIGS. 4 and 5). Suture retaining channel 159a is substantially aligned with the center of staple receiving pockets 133b so that upon firing of staples 127a, a portion of suture 129 is captured at various locations between staples 127a and the tissue, as described in more detail below. Suture retaining channel 159b extends parallel to channel 159a, but is offset from staple receiving pockets 133b so that a portion of suture 129 extends through channel 159b without being received within staples 127a during firing. This configuration allows suture 129 to form a substantially U-shape within lower cartridge 122a (discussed in more detail below and shown in FIGS. 3A and 5).

Upper cartridge 122b also includes an elongate body designed to fit within a longitudinal cavity in upper jaw 11 (not shown). Alternatively, the entire jaw 111 may comprise upper cartridge 122b. Similar to lower cartridge 122a, upper cartridge 122b includes a row of staples 127b supported on corresponding staple drivers or pushers 128b provided within staple receiving pockets 133c. Staple receiving pockets 133c may be cutouts that are partially or completely transverse to the longitudinal axis of end effector 110, and similar in length to the desired size of staples 127b to be fired. Upper cartridge 122b further includes suture retaining channels 159c, 159d that extend substantially parallel to the longitudinal axis of end effector 110 (see FIGS. 4 and 6B). Suture retaining channel 159c is substantially aligned with the center of the staple receiving pockets 133c so that upon firing of staples 127b, a portion of suture 129 is captured at various locations between staples 127b and the tissue, as described in more detail below. Suture retaining channel 159d extends parallel to channel 159c, but is offset from staples 127b so that a portion of suture 129 extends through channel 159d without being received within staples 127b during firing. This configuration allows suture 129 to form a substantially U-shape within upper and lower cartridges 122a, 122b (discussed in more detail below and shown in FIG. 3).

At least a portion of upper cartridge 122b is disposed over side 123b of lower cartridge 122a such that staples 127a, 127b are fired on either side of the end effector and suture 129 is captured between staples 127a, 127b and the tissue. This configuration allows for the placement of staples 127a, 127b and suture 129 around a tubular tissue or organ, such as bowel tissue, in the form of a purse string suture hoop, as discussed in more detail below. In certain embodiments, upper cartridge 122b fits into a longitudinal cavity on one side of jaw 111, and the other side of jaw 111 includes an anvil with staple forming pockets (not shown) for receiving linear staples 124. In other embodiments, the upper cartridge 122b includes the entire upper portion of jaw (including the anvil and staple forming pockets).

Figure 2E:
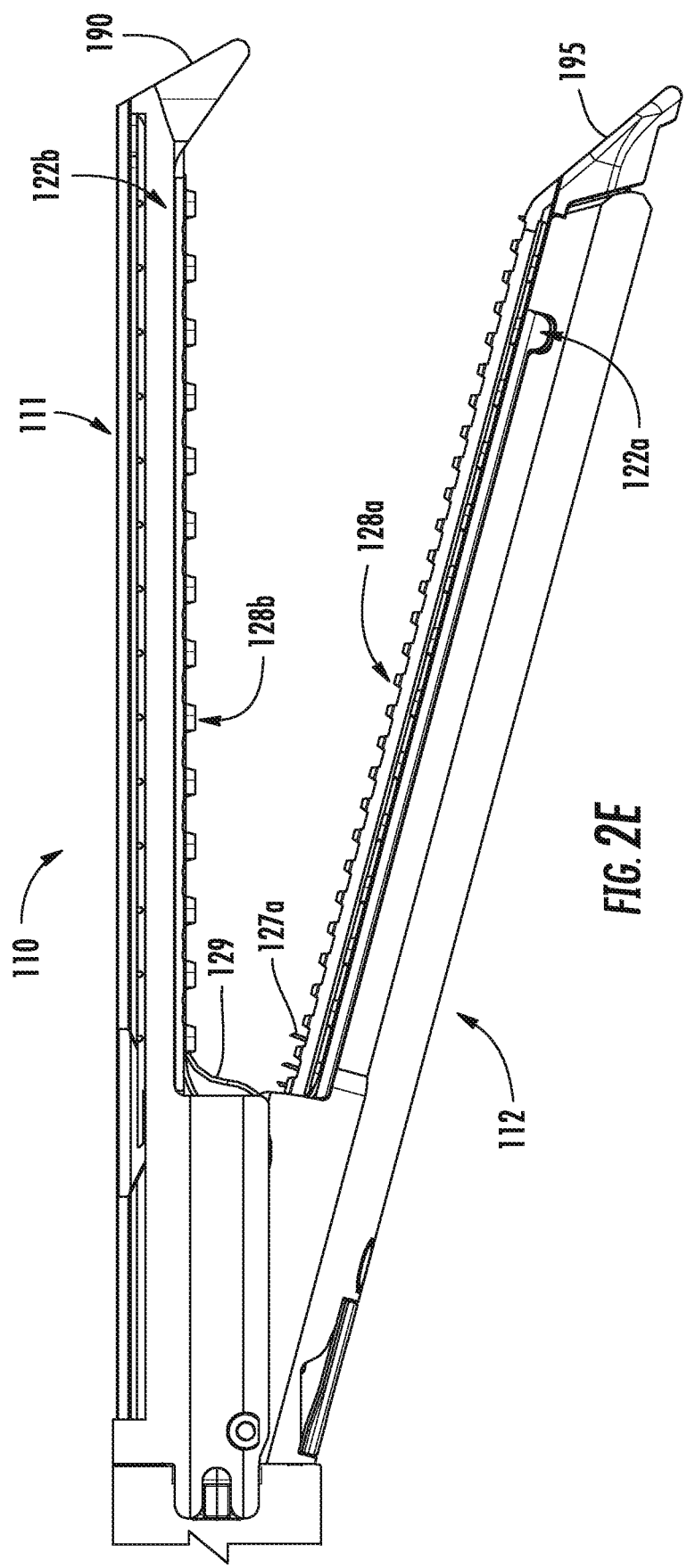
FIG. 2E is another side view of the end effector of FIG. 1, illustrating a position of staples in the jaws according to certain embodiments.

Referring now to FIG. 2E, staple drivers 128b in upper cartridge 122b are preferably offset in the longitudinal direction from staple drivers 128a in lower cartridge 122a. This allows staples 127a in lower jaw 112 to be positioned closer to staples 127b in upper jaw 111 in the pre-fired position (i.e., before the staples are driven into tissue). Offsetting the staples in this manner provides more space in the jaws, thereby providing a more compact and maneuverable instrument. Note that only one staple 127a is shown in FIG. 2E although it will be recognized that each of the staple drivers 128a, 128b has a corresponding staple coupled thereto.

As best shown in FIGS. 2A, 2B and 2E, in certain embodiments, upper jaw 111 (or in some embodiments, upper cartridge 122b) includes a distal end portion 190 that, upon closing of jaws 111, 112, overlaps a distal end portion 195 of lower cartridge 122a. Distal end portion 190 prevents cartridges 122a, 122b from sliding out of the jaws after installation. Distal end portion 190 may include a flexing latch member (not shown), that upon installation of cartridges 122a, 122b in jaws 111, 112 would engage with a recess (not shown) contained within jaw 111, retaining the latch member in place until defeated by application of finger pressure to release it. Flexure would provide an over-center snap feeling between the latched and the unlatched position, such that a surgeon would be able to feel the difference between the latched and unlatched positions. It is envisioned that the latch may be held in place by any number of desired mating features, such as a protrusion, or a cutout formed on jaw 111. In an alternative embodiment, cartridge 122a may further include cutouts or recesses configured to engage at least one hook or other protrusion contained within jaws 111, 112. Upon installation, cartridge 122a may slightly pivot such that the hooks catch within the recesses helping to retain the cartridge 122 in place.

Figure 10:
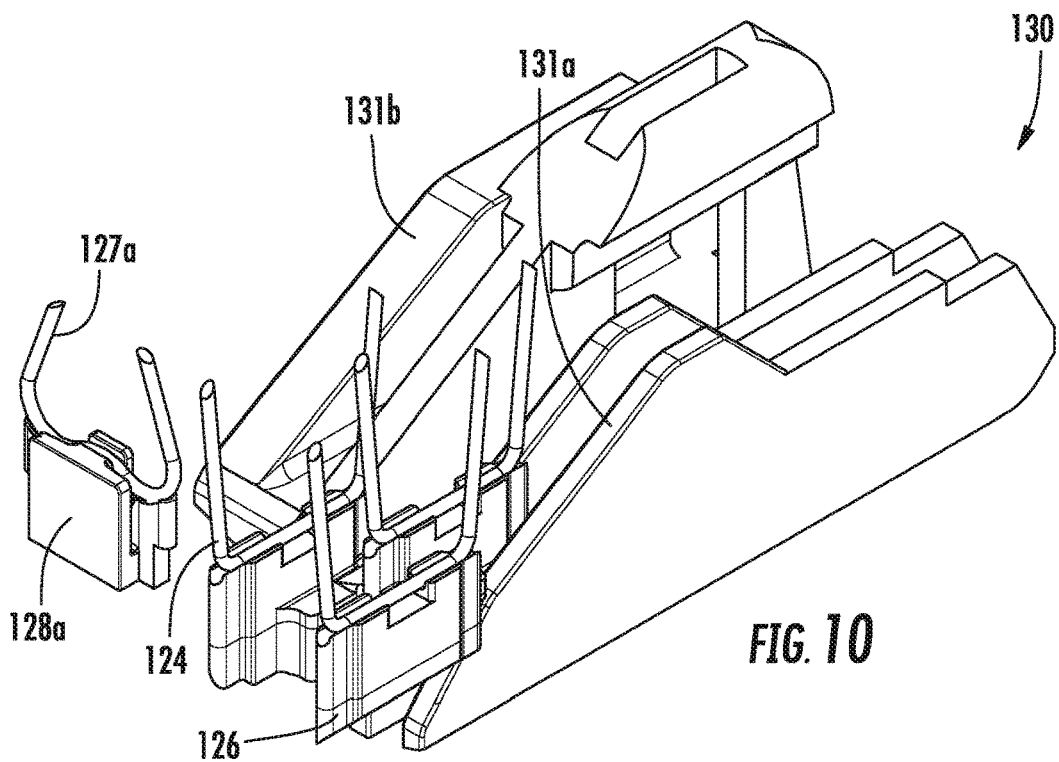
FIG. 10 is a perspective view of a shuttle for engaging staples within the staple cartridge.

As shown in FIG. 10, lower cartridge 122a also may include a shuttle 130 having one or more inclined distal portions 131a that, upon distal movement, sequentially acts on staple pushers 126, camming them towards grasped tissue thereby forcing staples 124 towards the grasped tissue. Shuttle 130 further includes inclined distal portion 131b that, upon distal movement, sequentially acts on staple drivers 128a, camming them towards grasped tissue thereby forcing staples 127a towards grasped tissue. The legs of staples 127a are positioned on either side of suture 129 and are configured to secure suture 129 to grasped tissue upon actuation of the surgical instrument. Details of the mechanism for formation of staples 127a, 127b to provide purse strings are described below.

Figure 3A:
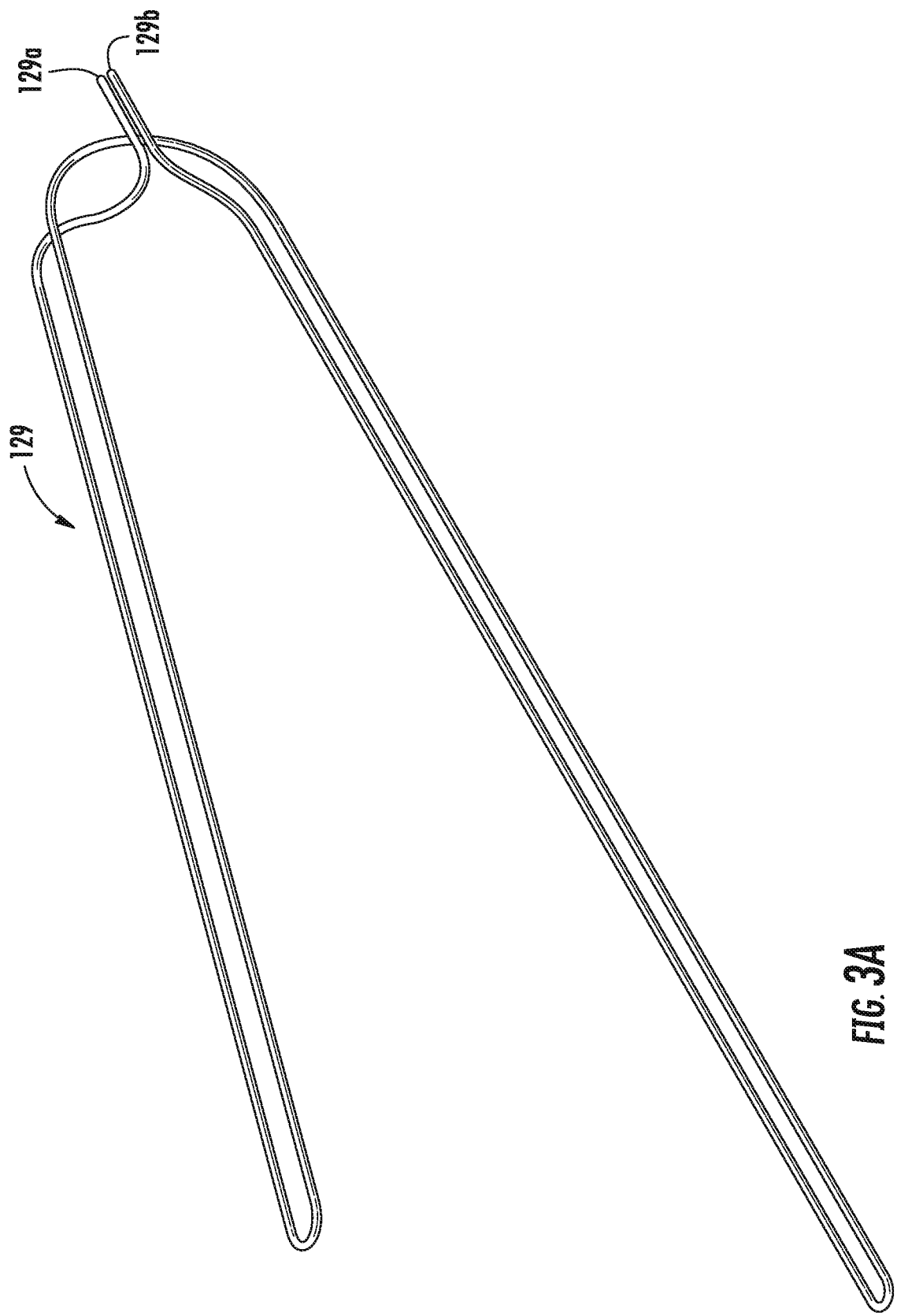
FIG. 3A is a perspective view of a suture configured in the shape that the suture is disposed in the end effector.
Figure 4:
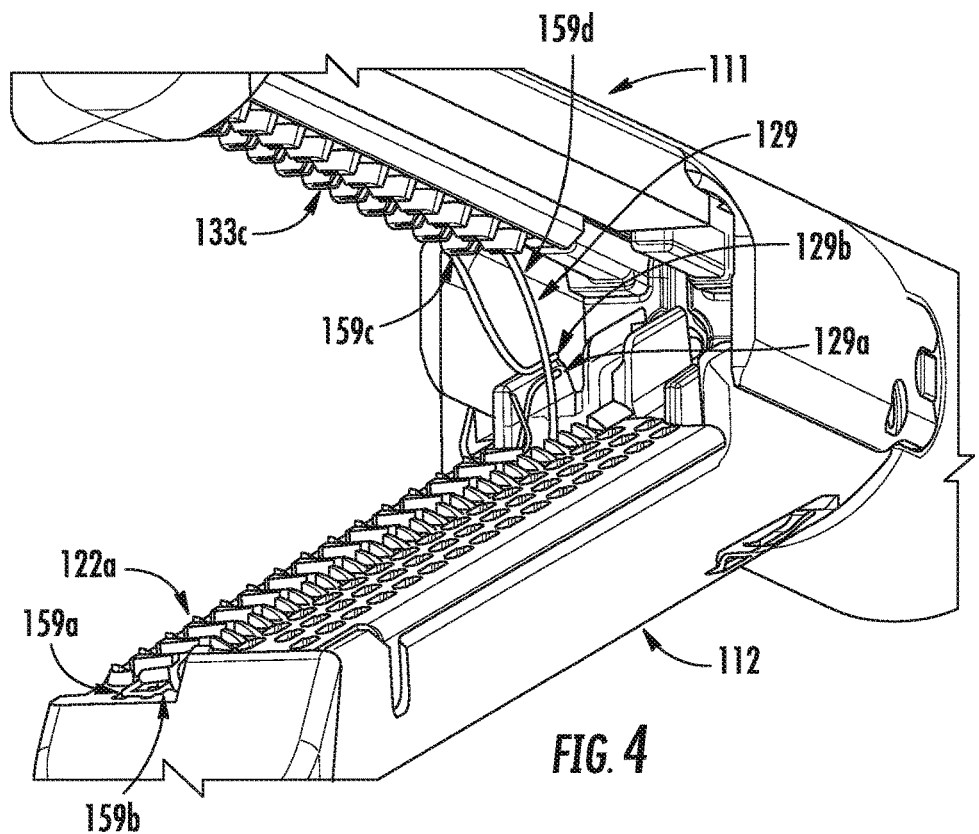
FIG. 4 is a perspective view of the jaws of the end effector of FIG. 1.
Figure 5:
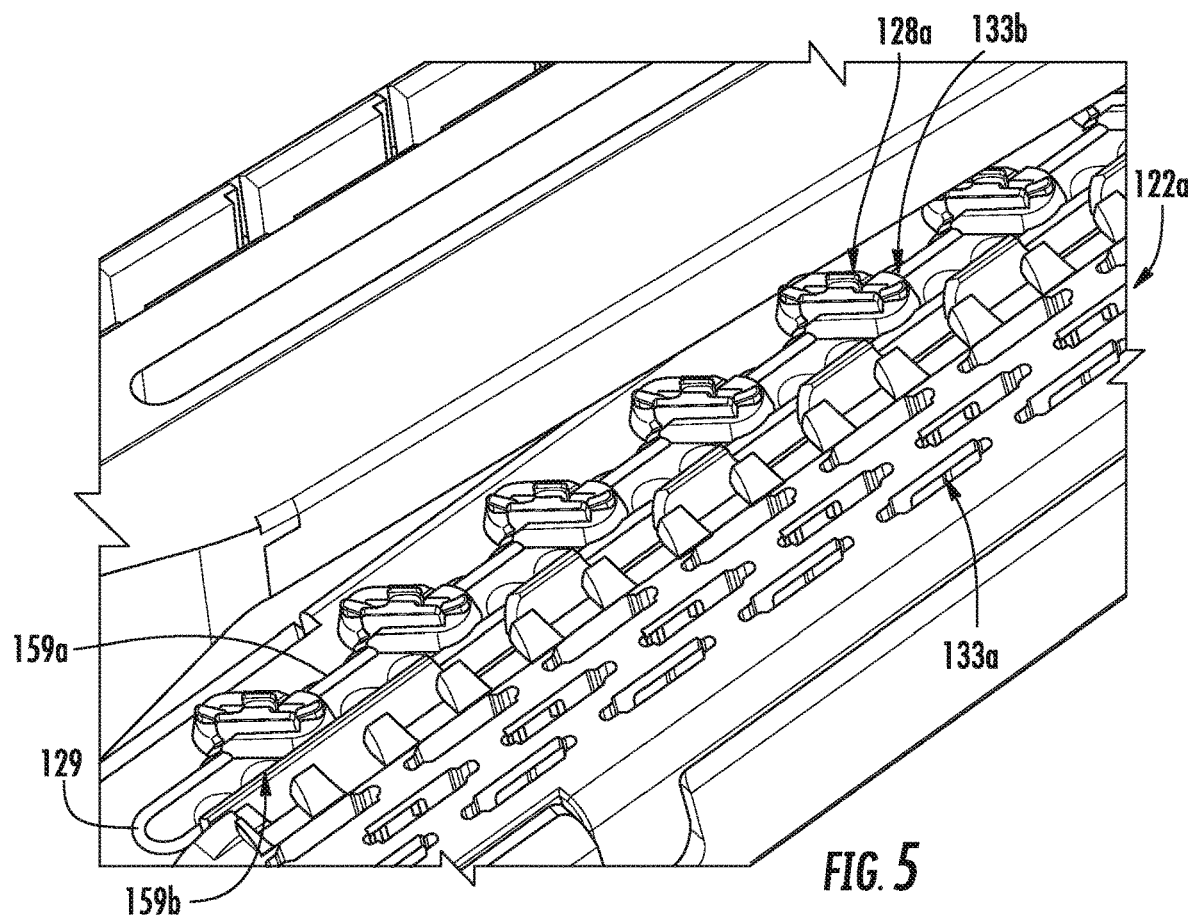
FIG. 5 is a close-up view of one of the jaws of FIG. 4, illustrating placement of a suture relative to a row of staples in the jaw.

Referring to FIGS. 3A and 4, suture 129 preferably includes first and second free ends 129a, 129b disposed proximal to the rows of staples 127a and 127b. In certain embodiments, suture 129 is designed to extend from one free end 129a through suture retaining channel 159a to a distal end of lower cartridge 122a such that it extends through sutures 127a. Suture 129 then forms a U-shape as it passes back through suture retaining channel 159b to the proximal end of lower cartridge 122a. From this point, suture 129 passes upwards into suture retaining channel 159d and extends to the distal end of upper cartridge 122b, where it reverses and passes proximally through suture retaining channel 159c to second free end 129b. In this manner, suture 129 can be installed into tissue between staples 127a, 127b such that it forms an open loop 630 on one side of the tissue and two free ends 129a, 129b on the other side (see FIGS. 31A and 31B). The two free ends 129a, 129b can then be pulled to tighten suture 129 around the tissue, as discussed in more detail below.

Figure 11A:
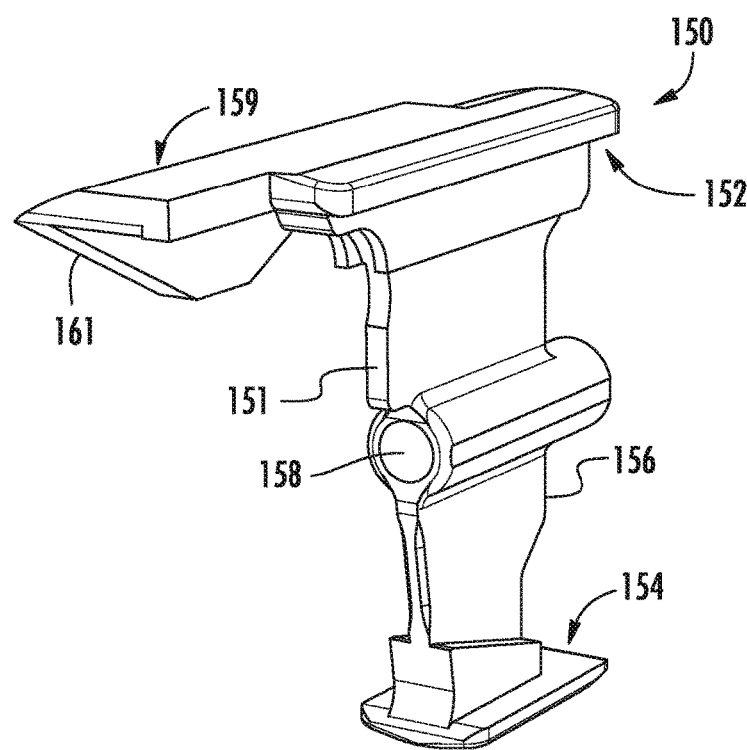
FIG. 11A is a perspective view of a drive member for actuating the end effector.
Figure 11B:
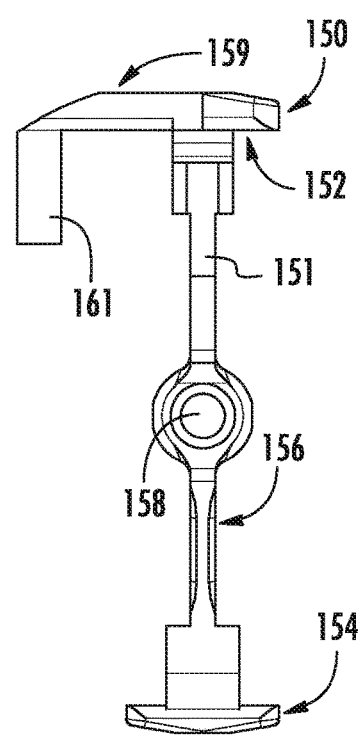
FIG. 11B is a front view of the drive member of FIG. 11A.
Figure 11C:
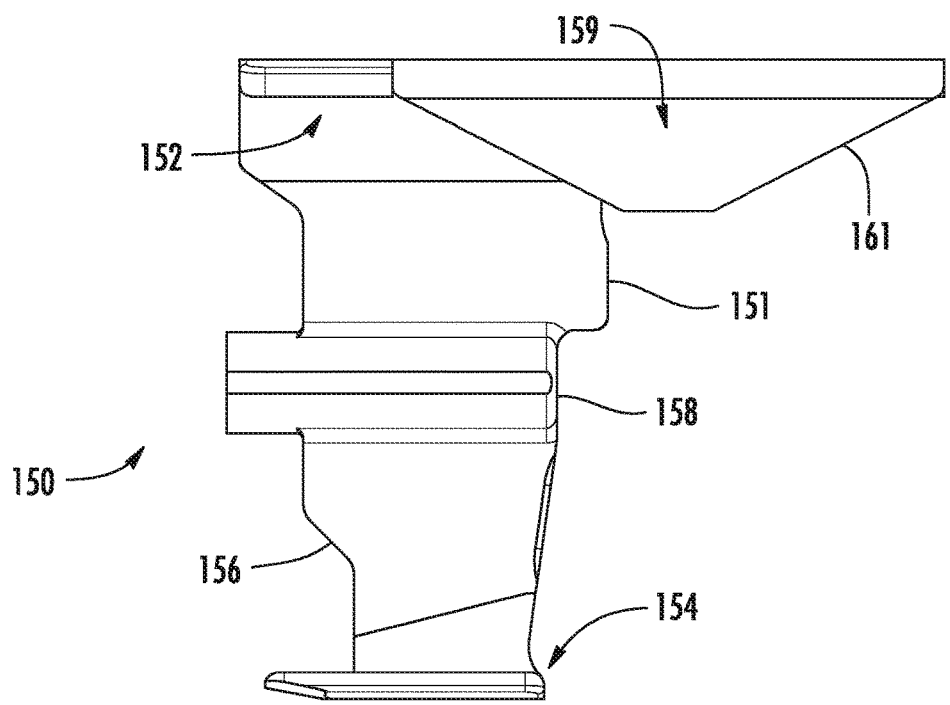
FIG. 11C is a side view of the drive member of FIG. 11A.

Referring now to FIGS. 11A-11C, a preferred embodiment of a drive member 150 may include a body, an upper shoe 152, a lower shoe 154, a central portion 156 and a lateral portion 159 coupled to, or integral with, upper shoe 152. Lower shoe 154 is configured to engage shuttle 130 as drive member 150 is translated distally through lower cartridge 122a. Lateral portion 159 includes a distal inclined surface or ramp 161 that engages with pushers 128b of upper cartridge 122b to drive pushers 128b (and the associated staples 127b) vertically or perpendicular to the longitudinal axis when drive member 150 is translated distally (see also FIG. 6B). In a preferred embodiment, lateral portion 159 is integrated into upper shoe 152 of drive member 150. Integrating lateral portion 159 into drive member 150 provides more flexibility in the design of staple cartridge 122b. For example, this may allow for a reduction in the size of staple cartridge 122b and surgical instrument 100.

Surgical instrument 100 further includes an actuation assembly that includes a drive cable (not shown) coupled to a drive rod (also not shown) that extends through a bore 158 in drive member 150. A more complete description of suitable actuation assemblies for surgical instrument 100 can be found in co-pending, commonly assigned PCT Application Nos. PCT/US2020/54568, filed Oct. 7, 2020, and PCT/US2020/20672, filed Mar. 2, 2020, the competed disclosures of which are incorporated herein by reference in their entirety for all purposes.

The drive cable is operationally connected to an actuator, which allows distal translation and proximal retraction of the actuation assembly and drive member 150. Drive member 150 may be coupled to any known actuation mechanisms including manually-activated actuators, motor-driven or powered actuators, or other types of actuation mechanisms. Those skilled in the art will recognize that in a manually actuated instrument, the actuator may be a movable handle; in a powered instrument the actuator may be a button (not shown) that causes a motor to act on the drive rod; and in a robotic system, the actuator may be a control device such as the control devices described below in connection with FIGS. 18 and 19. Any suitable backend actuation mechanism for driving the components of the surgical stapling instrument may be used. For additional details relating to exemplary actuation mechanisms using push/pull drive cables see, e.g., commonly assigned, co-pending International Application WO 2018/049217, the disclosure of which is hereby incorporated by reference in its entirety.

Upon actuation of surgical instrument 100, drive member 150 is pushed distally or pulled proximally through center knife channel 153 of cartridges 122a, 122b by the drive cable and the drive rod. Drive member 150 includes knife edge 151 positioned on main body 156 for severing clamped tissue upon distal translation of drive member 150 through center knife channel 153 during firing of surgical instrument 100. The central position of knife channel 153 ensures that knife edge 151 severs tissue that is adjacent to and between the two portions of tissue that are stapled and sutured, as discussed below.

The drive member is preferably configured to drive staples 127a, 127b into tissue such that suture 129, in combination with the staples, forms a purse string with the tissue. This is achieved by securing a purse string suture to the outer surface of the bowel via staples that pinch the surface of the bowel (discussed in further detail below). Simultaneously, drive member 150 drives staples 124 into tissue on the other side of knife edge 151 to form a linear staple line in the tissue.

Accordingly, the surgical instrument can simultaneously transect tissue, apply a linear staple line along one side of the tissue dissection with staples 124 and apply a suture 129, such as a purse string suture, to the other side of the tissue dissection (in combination with staples 127a, 127b). The tissue dissection allows for the two ends of the bowel to be separated for eventual removal of the resected specimen. The application of the linear staple line allows the user to close one end of the specimen to prevent content spillage. The application of a purse-string suture on the other end allows the user to cinch the bowel and prepare it for eventual anastomosis after the unwanted tissue has been removed. Performing all three of these functions with a single instrument makes the entire procedure faster, easier and more consistent for the user. In addition, it minimizes complications associated with crossing staple lines when used with an end-to-end circular stapler (e.g., during bowel resection procedures).

In certain embodiments, one of the jaws 110, 112 may include one or more indicia or visual markings one side of the jaw to differentiate the linear staple side from the purse string suture side of the jaw. The markings may be disposed on movable jaw 110, fixed jaw 112 or both. These markings allow the operator to easily visualize and differentiate the two different sides of the instrument during a surgical procedure so that the instrument can be properly oriented with respect to the tissue that will be dissected. In some embodiments, one side of the jaw, such as the linear staple side or the purse string suture side, have such markings or indicia and the other side has no markings. In other embodiments, both sides of the jaw have different markings to clearly differentiate one from the other.

The markings may include numbers (e.g., 1 for linear staple side and 2 for purse string suture or the reverse), letters (e.g., L and P or similar such letters), words, arrows, pictures, symbols, names, characters, shapes, graphics, colors and the like. For example, one side of the jaw could have the word staple and/or the other side of the jaw could have the word suture. Alternatively, one side of the jaw could be marked with a shape of a linear staple or a row of linear staples and/or the other side of the jaw could be marked with a shape of a purse string staple or a row of purse string staples. Alternatively, one side of the jaw could be marked with the overall configuration of the staples (i.e., parallel rows of linear lines indicating the linear staple side and/or a single non-linear line for the purse string side).

Figure 6A:
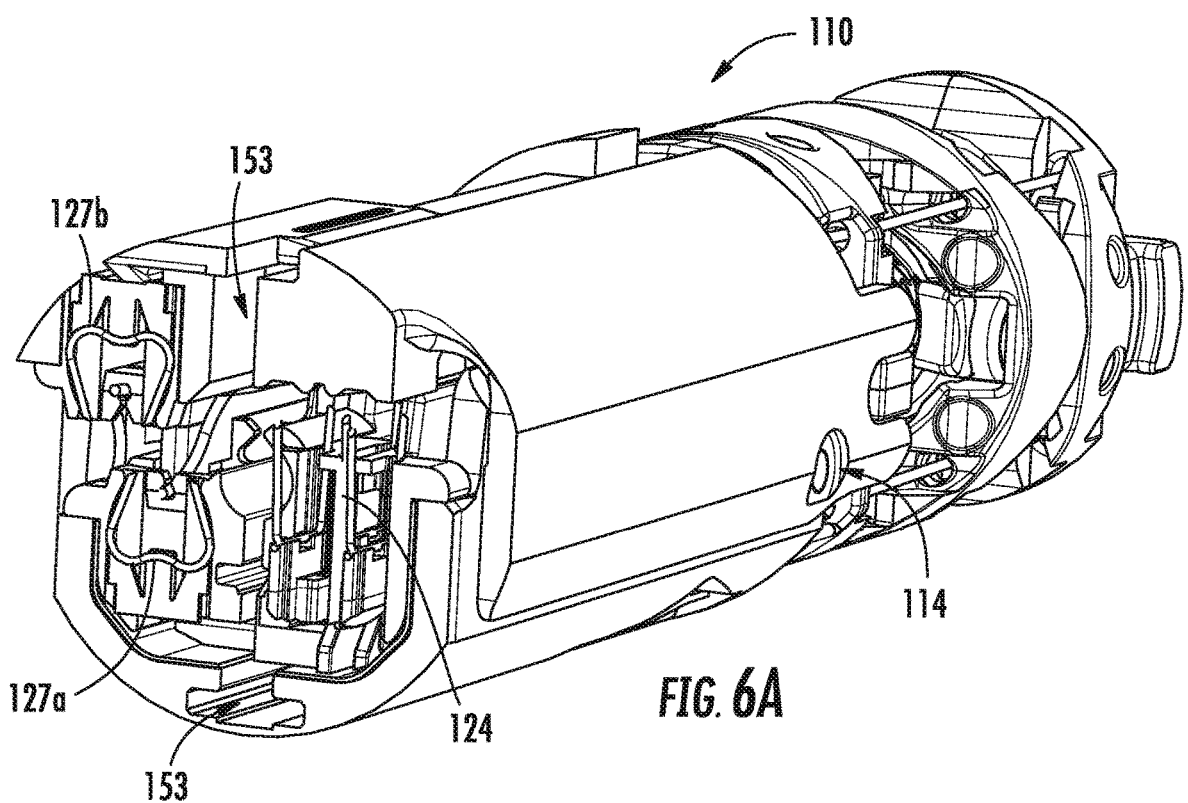
FIG. 6A is a partial cross-sectional and partial perspective view of one embodiment of an end effector.
Figure 7:
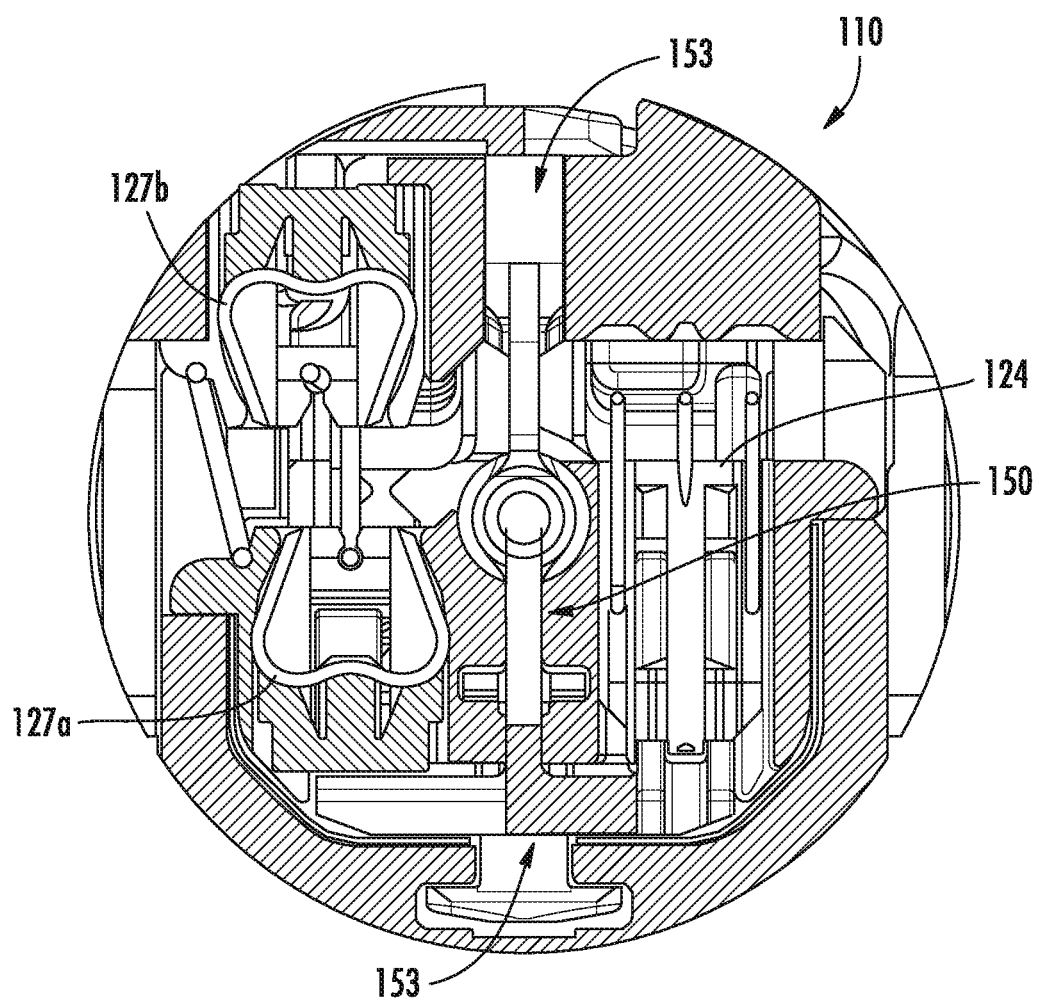
FIG. 7 is a cross-sectional view of the end effector of FIG. 1, illustrating a staple cartridge and a drive member for engaging staples within the staple cartridge.

One embodiment of a surgical instrument is shown in FIGS. 6A and 7. As shown, drive member 150 is configured to pass through center knife channels 153 of upper and lower suture cartridges 122a, 122b. Linear staples 124 are disposed laterally on one side of knife channel 153 and purse string staples 127a, 127b and suture 129 are disposed laterally on the other side of knife channel 153. In this embodiment, purse string staples 127a, 127b are laterally offset from each other such that lower staples 127a are disposed closer to knife channel 153 than upper staples 127b. In another embodiment, upper and lower staples 127a, 127b are offset from each other in the longitudinal direction such that each lower staple 127a is disposed between two upper staples 127b (see FIG. 2E). In some embodiments, upper and lower staples 127a, 127b are offset from each other both laterally and longitudinally. These embodiments allow staples 127a in lower jaw 112 to be positioned closer to staple 127b in upper jaw 111 in the pre-fired position (i.e., before the staples are driven into tissue). Offsetting the staples in this manner provides more space in the jaws, thereby providing a more compact and maneuverable instrument.

Figure 8A:
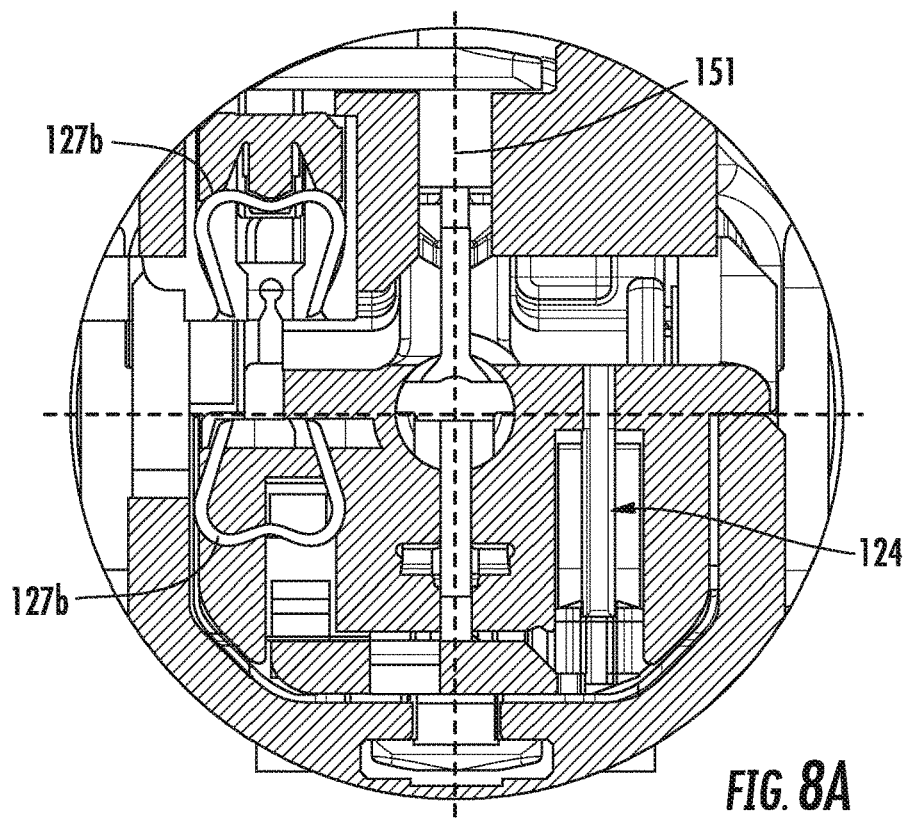
FIG. 8A is a cross-sectional view of another embodiment of the staple cartridge and the end effector.
Figure 8B:
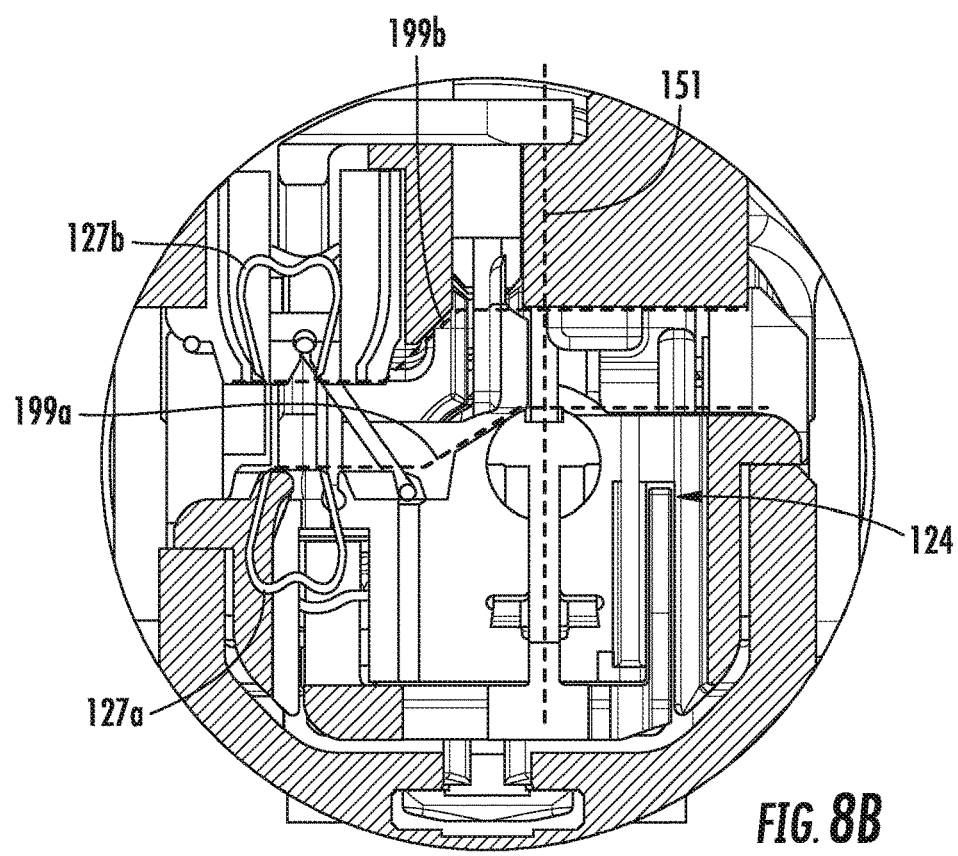
FIG. 8B is a cross-sectional view of another embodiment of the staple cartridge and the end effector.

FIGS. 8A and 8B illustrate alternative embodiments of surgical instrument 100. In the embodiment of FIG. 8A, staples 127a, 127b are disposed a substantially equal distance from knife channel 153 (i.e., they are not offset laterally from each other), but they are offset from each other in the longitudinal direction. In addition, the distance along tissue contacting surfaces 198a, 198b between purse string staples 127a, 127b and knife edge 151 is substantially equal to the distance along tissue contacting surfaces 198a, 198b and linear staples 124. Note that tissue contacting surfaces 198a, 198b are shown schematically with the dotted horizontal line in FIG. 8A.

Figure 6B:
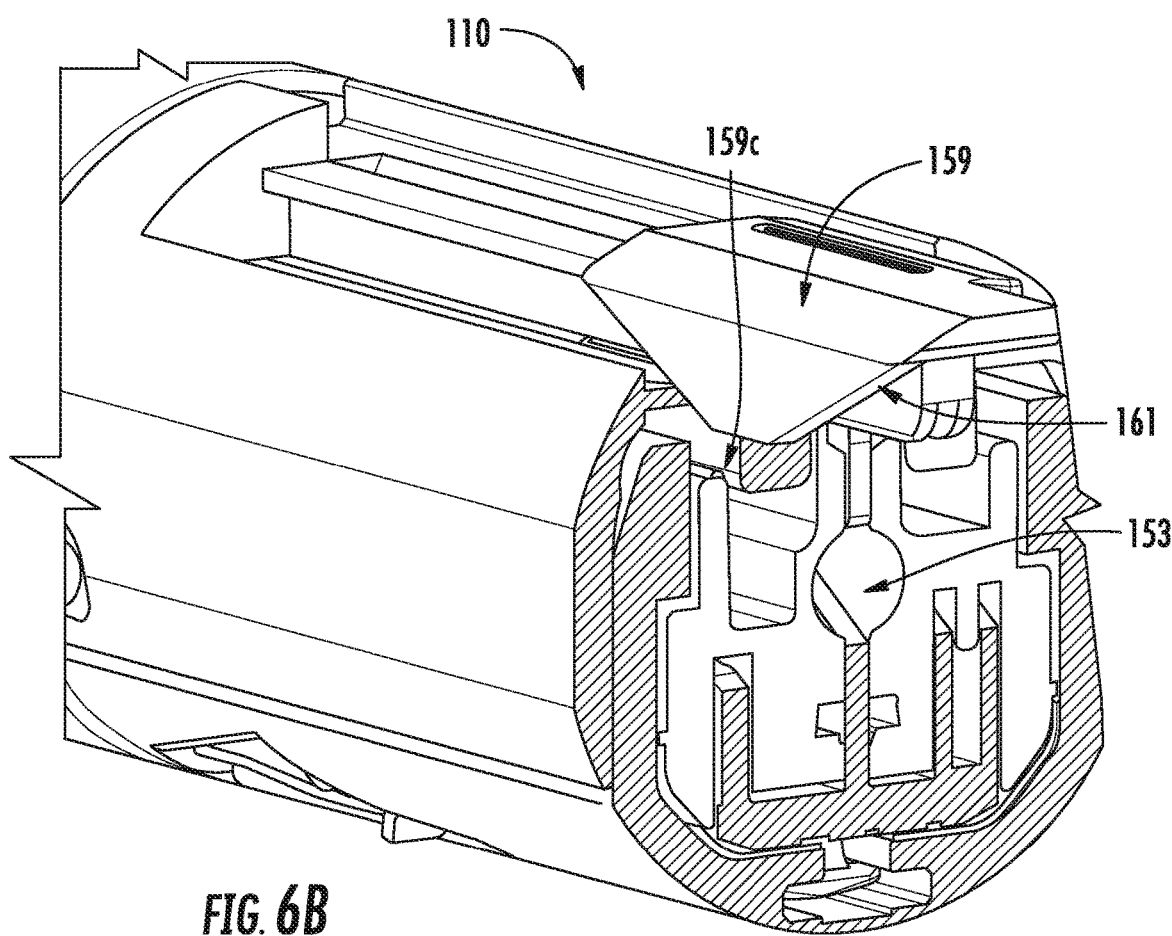
FIG. 6B is a partial cross-sectional and partial perspective view of the end effector of FIG. 6A with parts removed.

In the embodiment of FIG. 8B, the distance along tissue contacting surfaces 198a, 198b (shown as the dotted horizontal lines) between purse string staples 127a, 127b and knife edge 151 is greater than the distance along tissue contacting surfaces 198a, 198b and linear staples 124. Knife edge 151 is shown schematically as the dotted vertical line in FIG. 8B. This increases the amount of "tissue cuff" between the resection plane (i.e., the line of dissection from knife edge 151 of drive member 150) and the purse string staples 127, thereby minimizing complications between the purse string staples and the circular stapler during the anastomosis. Note that although only one row of linear staples 124 is shown in FIG. 6B, it will be recognized that the instrument may contain more than one row, as is shown in FIG. 8A.

In certain embodiments, purse string staples 127a, 127b are disposed at a transverse angle to the longitudinal axis of end effector 110 such that one leg of each staple is disposed distally of the other leg. As shown in FIGS. 2D and 8B, this configuration moves purse string staples 127a, 127b laterally away from the longitudinal axis of end effector 110 and the knife edge 151, thereby increasing the width of the tissue therebetween.

In other embodiments, knife channel 153 is laterally offset from the central longitudinal axis of end effector 110 towards staples 124. This disposes the knife channel 153 closer to linear staples 124 than purse string staples 127a, 127b, thereby increasing the width of tissue between the line of dissection and the purse string staples 127a, 127b.

In yet another embodiment, upper and lower jaws 111, 112 each comprise an angled portion 199a, 199b on their tissue contacting surfaces 198a, 198b that extends downwardly from knife channel 153 towards purse string staples 127a, 127b. This creates a jog in the plane in which the tissue sits between the jaws 111, 112 of the device, thereby increasing the distance along tissue contacting surfaces 198a, 198b between knife channels 153a, 153b and staples 127a, 127b.

Of course, it will be recognized that the devices disclosed herein are not limited to one or all of the above embodiments. For example, the end effector 110 may comprise all of these embodiments or any combination of these embodiments; i.e., jogged tissue plane and angles staples, angles staples and knife channels 153 offset from the axis, etc. Alternatively, the tissue cuff between the knife channels and the purse string staples may be increased in other ways, such as increasing the size of end effector 100, decreasing the number of rows of linear staples 124 and the like. However, the embodiments of the disclosed herein have the advantage of increasing the tissue cuff without having to increase the size of end effector and/or reduce the number of rows of linear staples 124.

Figure 9:
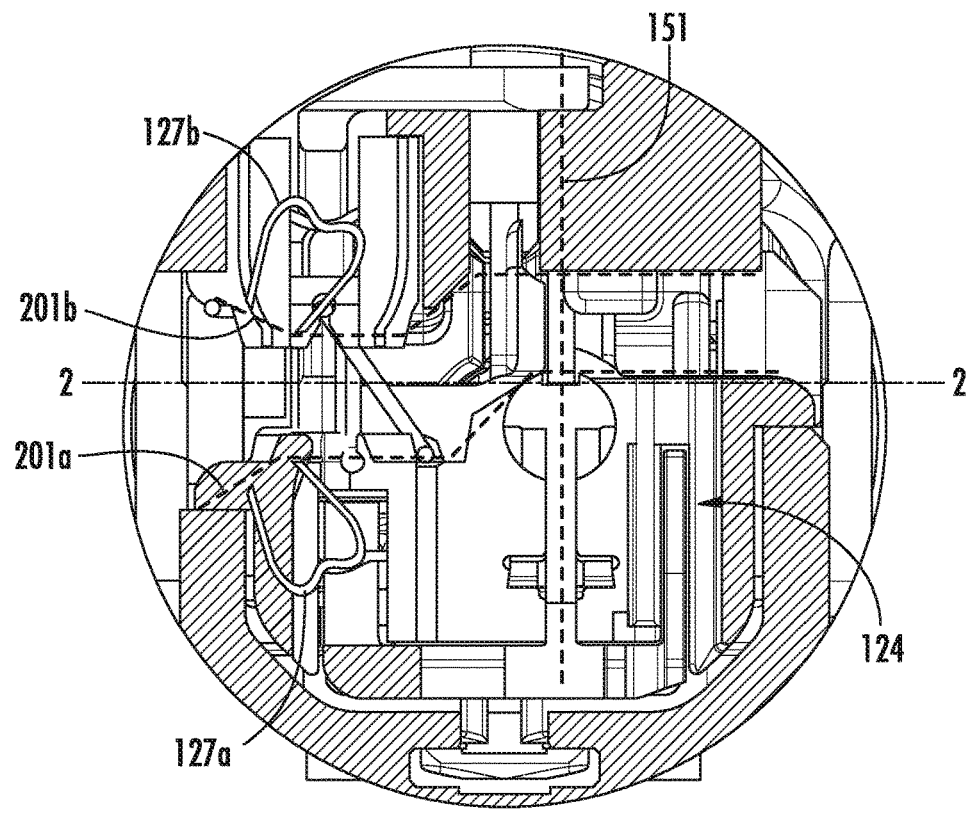
FIG. 9 is a cross-sectional view of yet another embodiment of the staple cartridge and the end effector.

FIG. 9 illustrates yet another embodiment of an end effector 110. In this embodiment, purse string staples 127a, 127b may be disposed at a transverse angle to the longitudinal axis of end effector 110 as in the previous embodiment shown in FIG. 8B. In addition, or in the alternative, staples 127a, 127b are disposed at a transverse angle to a lateral axis of shaft (2-2) such that one leg of each staple is higher than the other leg of the staple. In addition, tissue contacting surfaces 198a, 198b have a second angled portion 201a, 201b. Angled portion 201a extends downwards towards jaw 112 angled portion 201b extend upwards towards jaw 111. This configuration further increases the distance along tissue contacting surfaces 198a, 198b between knife channel 153 and staples 127a, 127b.

Figure 12:
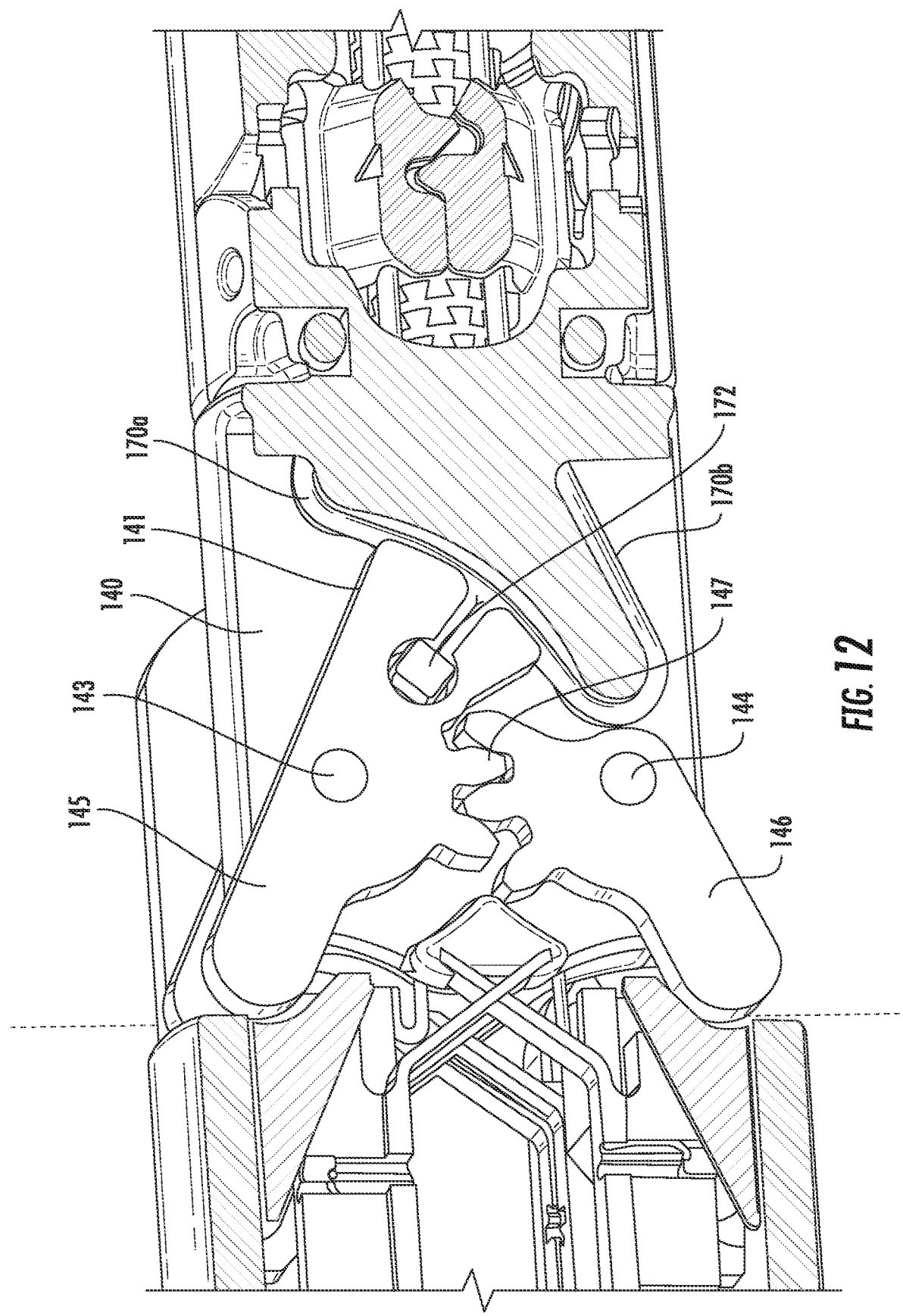
FIG. 12 is a partial cross-sectional view of the jaw closure mechanism of the surgical instrument of FIG. 1.

FIG. 12 shows a portion of surgical instrument 100 configured to open and close the jaws including clevis 140, first link member 145, second link member 146, and drive cables 170a, 170b. As shown, two drive cables 170a, 170b route symmetrically to the backend of surgical instrument 100, and terminate in a knot 172 within the proximal end 141 of a first link member 145. As cables 170a, 170b are pulled by the force of the motor (not shown) or via some other mechanism, first link member 145 rotates about pivot pin 143 on clevis 140, causing a second link member 146 to rotate about pivot pin 144 on clevis 140, thereby moving the jaws towards an open or closed position depending on which drive cable was pulled. The resulting jaw force is substantially similar to the cable pull force. One of ordinary skill will appreciate that a pair of drive cables may be present on each side, of surgical instrument 100, each pair of drive cables including a first cable for closing a first link, and a second cable for opening the first link. Using four cables in total for opening and closing of the jaw reduces the stress on each cable, and allows for symmetrically balanced cable forces through the wrist 160 such that actuating the jaw does not impart pitch or yaw forces into the wrist. (See FIG. 10.)

Figure 13:
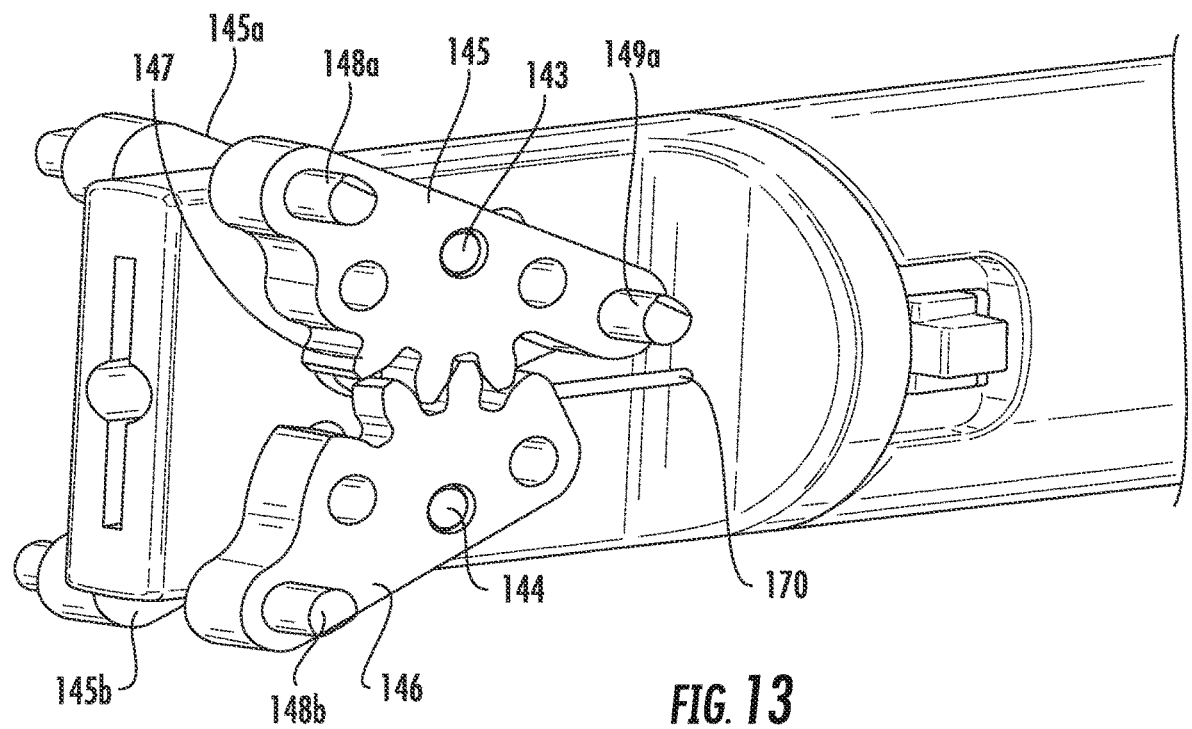
FIG. 13 is a perspective view of the first and second links of the jaw closure mechanism.
Figure 14:
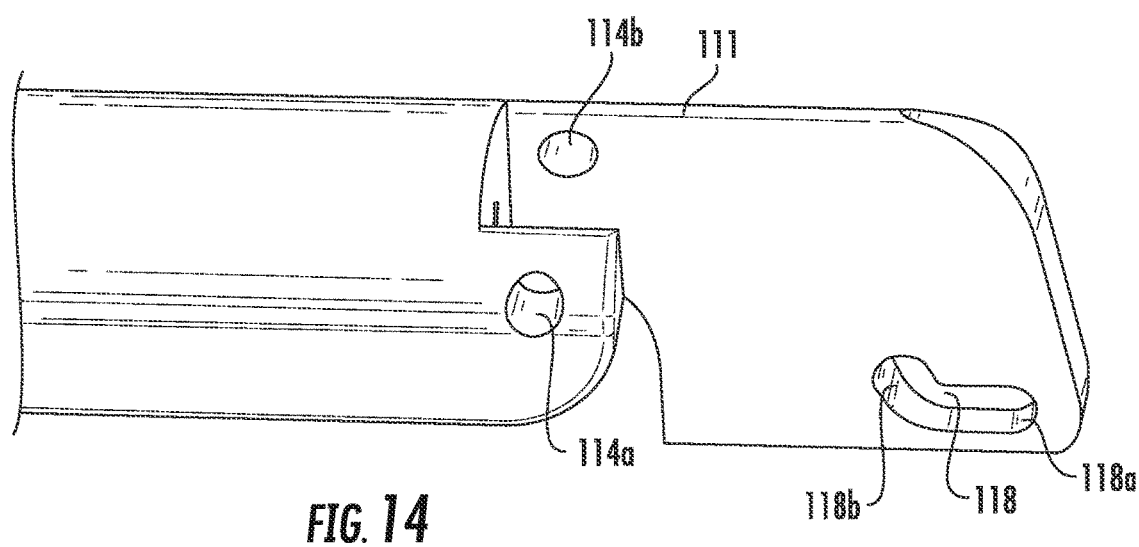
FIG. 14 is a perspective view of a portion of a jaw of the surgical instrument of FIG. 1.

As illustrated in FIGS. 13 and 14, link member 145 includes upper outer pin 148a, and link member 146 includes lower outer pin 148b. Upper outer pin 148a is configured to be positioned within an opening of jaw 111 (not shown), while lower outer pin 148b is configured to be positioned within an opening of jaw 112. Link member 145 also include cam slot pin 149a configured to engage and ride within cam slot 118 formed on jaw 111. Cam slot 118 is designed such that the proximal portion 118a of cam slot 118 allows for parallel closure of jaw 111, while the distal portion 118b of cam slot 118 allows for angular closure of jaws 111 upon rotation of link members 145, 146 due to the force of the drive cable 170a, 170b upon actuation of the surgical instrument (see FIG. 15). A second set of link members 145a, 145b and corresponding openings and cam slot, similar to link members 145, 146 is present on the far side of clevis 140 jaws 111, 112 and function similarly to link members 145, 146. Links members 145, 146 also include gear teeth 147 to enforce equally symmetric motion of jaws 111,112.

FIG. 15 illustrates the articulation mechanism including an articulating wrist 160, and drive cables 170c, 170d running from the proximal end of the instrument to wrist links 162, 164. Wrist 160 includes a number of links that provide a desired amount of motion, such as +/−90 degrees in a pitch or yaw direction. In embodiments, a single joint can provide up to a 90 degree angular deflection. According to an exemplary embodiment, a wrist may include a plurality of links to achieve higher ranges of motion, such as, for example, wrists having a range of motion of up to +/−180 degrees in a pitch or yaw direction. Typically, actuation elements such as, for example, pull/pull tendons or push/pull rods, and electrical conductors that are connected to a wrist and/or end effector of an instrument may extend through the elongated shaft of the instrument. Further, the actuation elements may extend through the elongated shaft and connect to a transmission mechanism that typically provides a mechanical coupling of the drive tendons to drive motors. As noted above, surgical instrument 100 may include two pairs of drive cables for opening and closing of the jaws, reducing the stress on each cable, and allowing for symmetrically balanced cable forces through wrist 160 such that actuating the jaw does not impart pitch or yaw forces into the wrist. Additionally, it is envisioned that the cables may merge within the mid-section of surgical instrument 100 such that only two cables are presented at the input capstans (not shown). This type of merging allows for a pulley to maintain cable length conservation as the wrist pitches or yaws. Additional details of other joints and wrist actuation elements usable with the embodiments disclosed herein, are disclosed in Int'l. Pub. No. WO 2015/127250A1, the entire disclosure of which is incorporated by reference herein.

Figure 16:
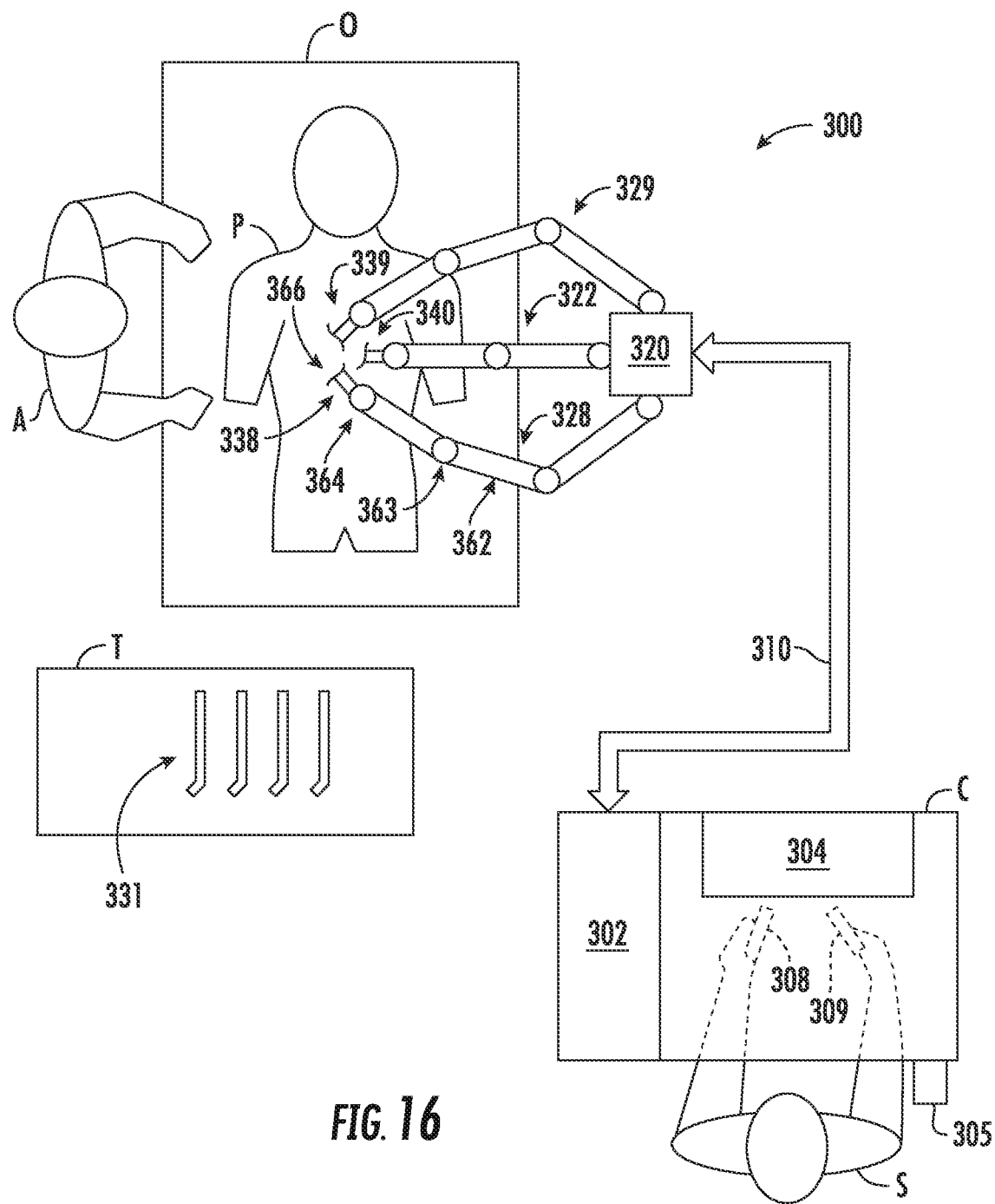
FIG. 16 illustrates a top view of an operating room employing a robotic surgical system.

The present surgical instrument for applying one or more purse string sutures may be used in a robotic surgical system. FIG. 16 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One important function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware.

For additional details on robotic surgical systems, see, e.g., U.S. Pat. Nos. 6,493,608 and 6,671,581, the entire contents of which are incorporated herein by this reference.

Figure 17:
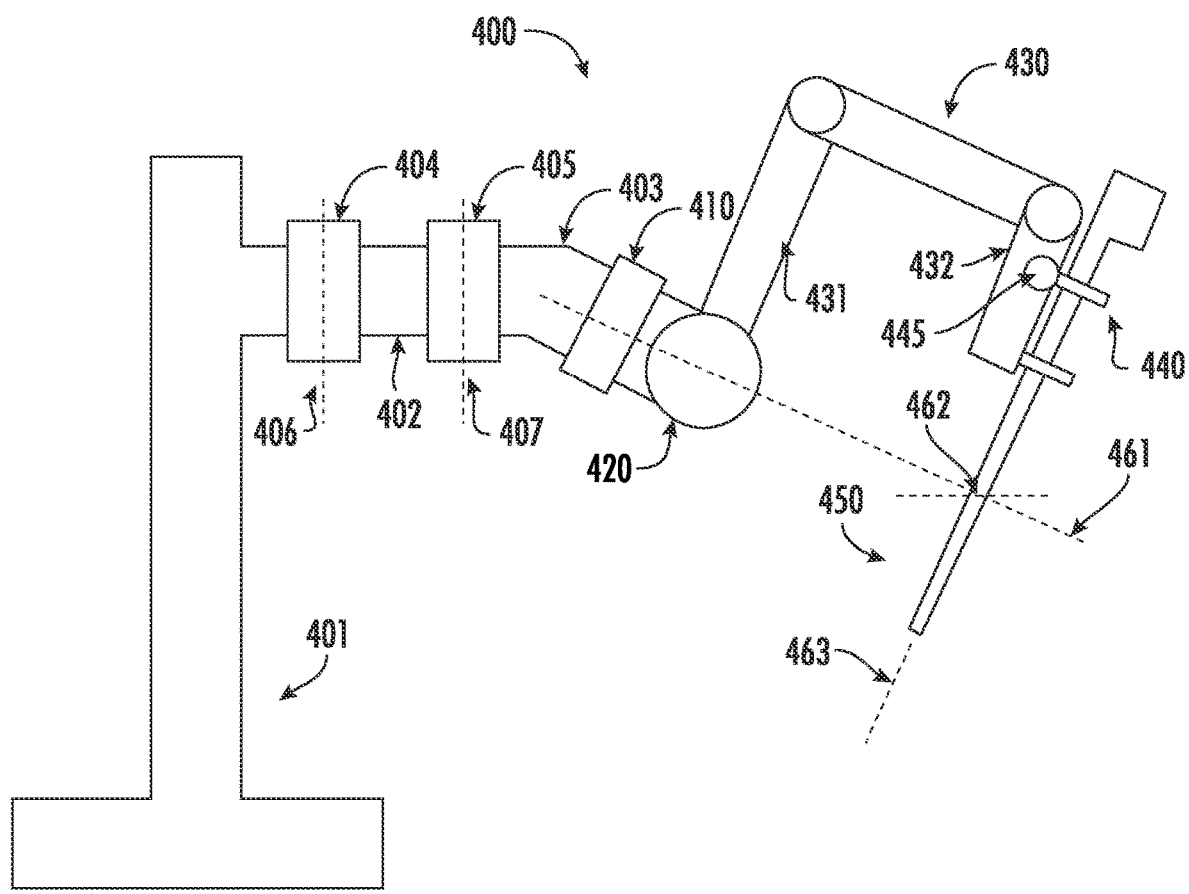
FIG. 17 illustrates a simplified side view of a robotic arm assembly that is usable various devices disclosed herein.

FIG. 17 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403 which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407.

Although only two links and two setup joints are shown in this example, more or less of each may be used as appropriate in this and other robotic arm assemblies in conjunction with the devices disclosed herein. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator.

Figure 18A:
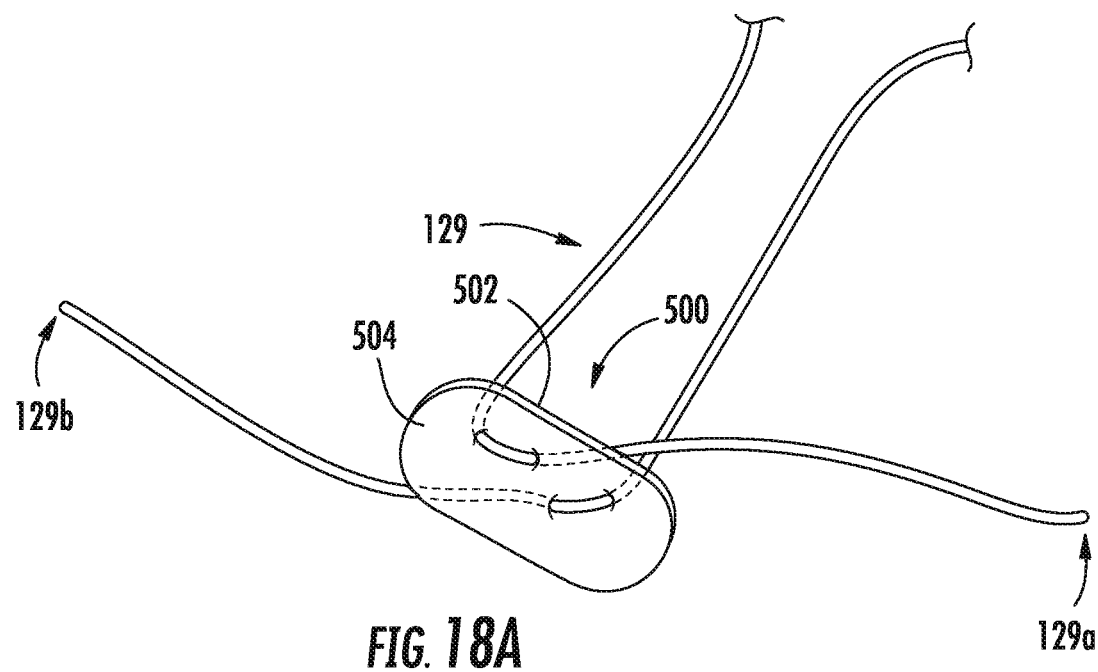
FIG. 18A illustrates a suture holding member for retaining a suture against tissue.
Figure 18B:
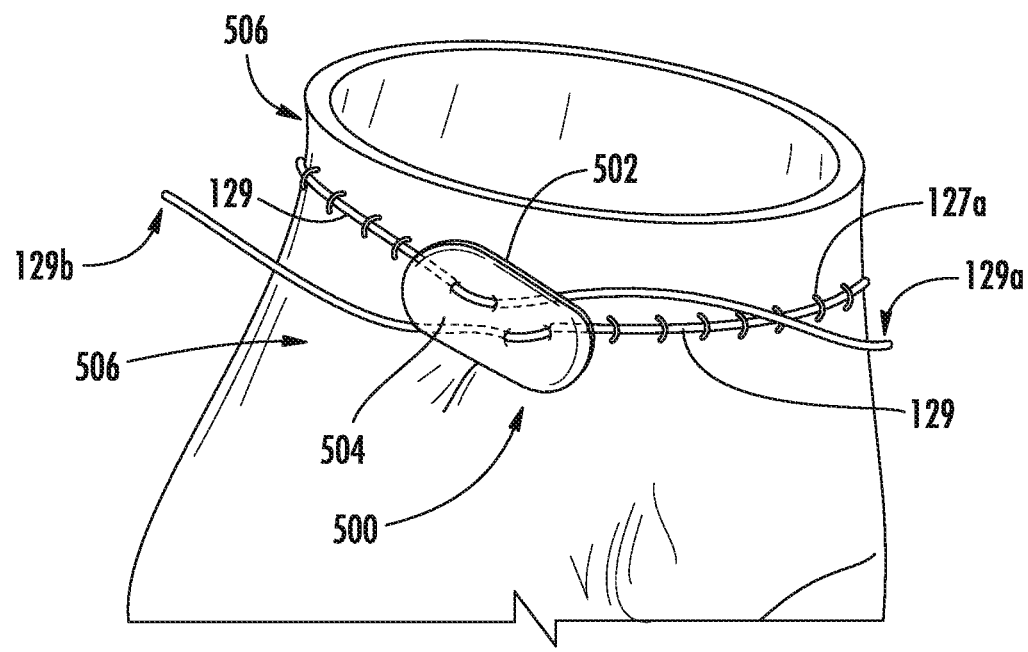
FIG. 18B illustrates the suture holding member of FIG. 18A being used to cinch representative tissue.

Referring now to FIGS. 18A and 18B, in another aspect, a suture holding member 500 comprises one or more openings for receiving suture 129 therethrough. In certain embodiments, suture holding member 500 is disposed within end effector 100 such that at least one of the free ends 129a, 129b of the suture is coupled to suture holding member 100. Suture holding member 500 allows the user to apply a purse string hoop around tissue 506 without having to tie knots to hold the purse string hoop tight, thereby making the procedure easier, faster and more consistent than conventional procedures. In addition, suture holding member 500 provides some degree of compliance to the purse string hoop, such that the purse string has some "give" when the circular stapler spike and/or anvil post enters the purse string hoop. This minimizes or eliminates rupture of the purse string suture when the circular stapler is performing the anastomosis.

In certain embodiments, drive member 150 is configured to translate distally through the first and second jaws 111, 112 to drive purse string staples 127a, 127b into tissue such that suture 129 extends between the staples 127a, 127b and tissue 506. Suture holding member 500 has a tissue contacting surface 502, and a second surface 504 opposite tissue contacting surface 502. Suture holding member 500 is disposed within end effector 110 such that second surface 504 faces a distal end of end effector 110 when staples 127a, 127b have been driven into tissue 506 (see also FIGS. 29A and 29B). In this manner, suture holding member 500 will be facing the instrument after the purse string hoop has been applied to the tissue. This allows the user to immediately visualize suture holding member 500 after the purse string hoop has been applied to the tissue, thereby making it easier to tighten down the suture holding member (e.g., without having to search for the suture holding member on the other side of the bowel).

In a preferred embodiment, first and second jaws 111, 112 each comprise suture retaining channels 159a, 159b, 159c, 159d for receiving a portion of the suture that is substantially parallel with the row of staples, as discussed above and shown in FIG. 4. Suture holding member 500 is disposed proximal to the row of staples 127a, 127b within end effector 110. Suture 129 extends from the suture holding member 150 distally through the row of staples in the first jaw, proximally through the channel in the first jaw, distally through the channel in the second jaw and then proximally through the row of staples in the second jaw such that the second free end is disposed proximally of the first row of staples. Thus, the suture forms a substantially U-shape in each of the first and second jaws, thereby allowing a user to apply the suture and suture holding member to tissue with the instrument such that the suture holding member is facing the instrument.

As shown in FIGS. 18A and 18B, suture holding member 500 is configured such that both first and second free ends 129a, 129b of the suture extend therethrough. This allows the user to easily tighten down the purse string hoop simply by holding suture holding member 500 and pulling the frees ends 129a, 129b of the suture. In this embodiment, suture 129 extends through openings in suture holding member 500 such that the first and second free ends 129a, 129b extend substantially tangential to tissue contacting surface 502. Thus, the suture 129 extends through suture holding member 500 such that the first and second free ends 129a, 129b extend away from suture holding member 500 in substantial opposite directions from each other. This minimizes the tension on the adjacent staples as the suture 129 is tightened, i.e., suture holding member 500 acts as a passive pulley that absorbs at least some of force applied by the sutures as they are pulled and tightened.

In certain embodiments, suture 129 is coupled to suture holding member 500 with a friction fit configured to release under a threshold level of tension. This allows suture holding member 500 to hold the suture when tightened down and generally manipulated, but would release under some level of tension. For example, as the circular stapler enters the purse string hoop and stretches it wider, suture holding member 500 will release if the tension level becomes sufficiently high to rupture the purse string hoop.

In one such embodiment, suture holding member 500 comprises a compliant material, such as rubber or a similarly compliant material. In other embodiments, suture holding member 500 is designed with compliant features to allow such functionality. In an exemplary embodiment shown in FIGS. 18A and 18B, suture 129 is woven through suture holding member 500 to create friction between suture 129 and holding member 500. This friction is preferably strong enough to generally maintain a strong enough hold on tissue 506 to keep the tissue cinched after it has been dissected, but compliant enough to minimize or avoid rupture of the purse string hoop during the anastomosis (discussed in detail below).

Referring now to FIGS. 19A and 19B, another embodiment of a suture holding member 510 will now be described. As shown, suture holding member 510 comprises a tissue contacting surface 512 and suture 129 extends through channels 514 in suture holding member 510 such that first and second free ends 129a, 129b extend substantially radially to tissue 506. Thus, suture 129 extends through suture holding member 510 such that the first and second free ends extend away from suture holding member 510 in substantial the same direction. This allows the user to tighten the purse string suture via a surgical "draw down" technique in which one hand holds suture holding member 510 down, while the other hand pulls both suture ends 129a, 129b away from holding member 510.

FIGS. 20A-20C illustrate other embodiments for providing some degree of compliance to suture holding member 500. As shown, suture holding member 500 includes a locking element 520 that forces suture 129 to be routed through a non-linear path from the opening of suture holding member 500. This provides sufficient resistance to movement of the suture 129 to hold the suture in place while cinching the tissue. However, locking element 520 provides some degree of compliance such that suture 129 may release under a threshold level of tension, e.g., when the bowel is being opened up during the anastomosis. This embodiment allows the user to feed suture 129 through suture holding member 510, while locking element 520 "auto locks" the position of the suture.

Figure 21:
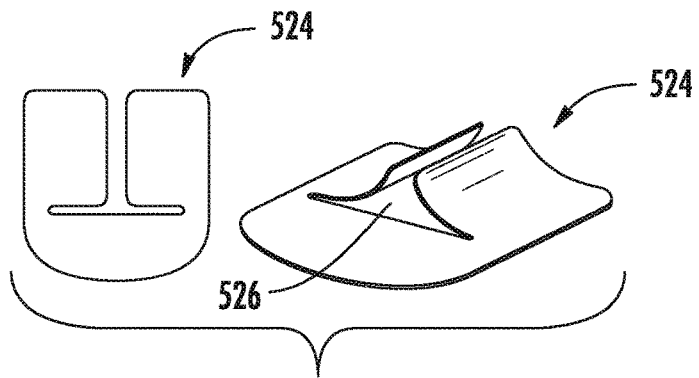
FIG. 21 illustrates another embodiment of a suture holding member with a locking element.

FIG. 21 illustrates another embodiment of a suture holding member 524 that includes a locking element 526. Similar to the previous embodiment, suture 129 can be feed through suture holding member 524 while locking member 526 auto locks suture 129 in position, while still maintaining sufficient compliance to allow expansion of the tissue during, for example, an anastomosis procedure.

Figure 22:
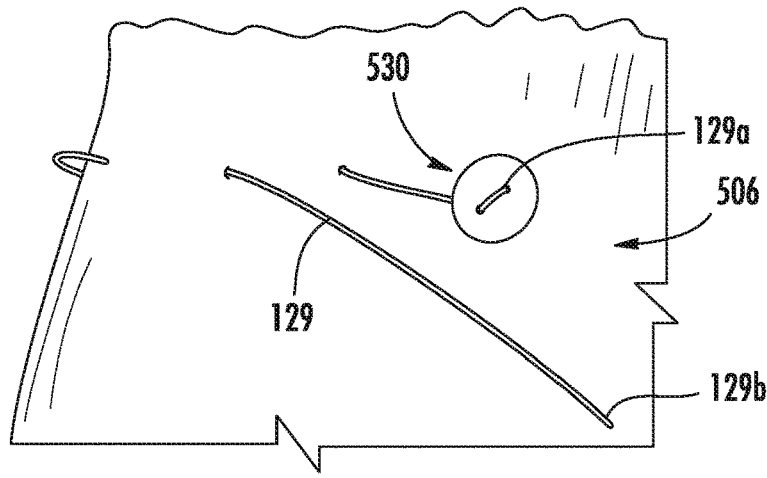
FIG. 22 illustrates a wrap-around suture holding member.

FIG. 22 illustrates another embodiment of a suture holding member 530. As shown, one end 129a of suture 129 is coupled to a suture holding member 530 while the other free end 129b remains unattached to suture holding member 530. This "wrapping anchor" design allows the user to take one free end of the suture and wrap it around the base of suture holding member 530, and pull to tighten the suture and cinch the tissue. The wrapping of the suture causes the purse sting hoop to tightly hold together. The suture may be coupled to suture holding member 530 in a variety of methods, such as tying, weaving and the like.

Figure 23:
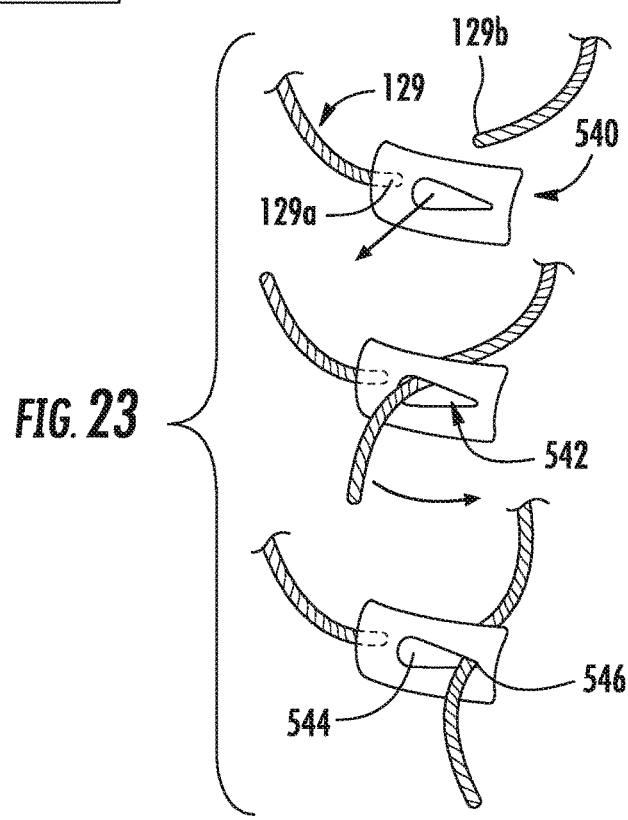
FIG. 23 illustrates a "feed and cinch" embodiment of a suture holding member.

As shown in FIG. 23, another embodiment of a suture holding member 540 comprises an opening 542 for receiving one of the free ends 129b of suture 129. The other free end 129a may be coupled to suture holding member 540 in any of the methods discussed above. Opening 542 includes an enlarged region 544 for passing the free end of suture 129 therethrough, and a narrowed slot 546 for securing the free end of the suture to suture holding member 540. This allows the user to feed the free end of the suture into the opening 542, cinch the purse string hoop tight, and then draw the suture into the narrowed slot 546 to secure the suture and keep the purse string hoop tight throughout the remainder of the procedure.

Figure 24:
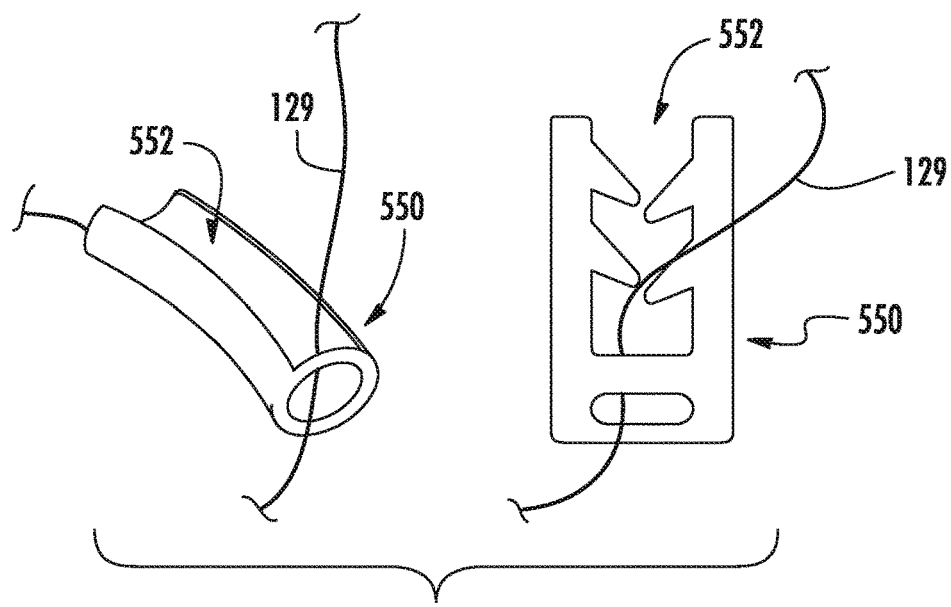
FIG. 24 illustrates another embodiment of a "feed and cinch" suture holding member.
Figure 25:
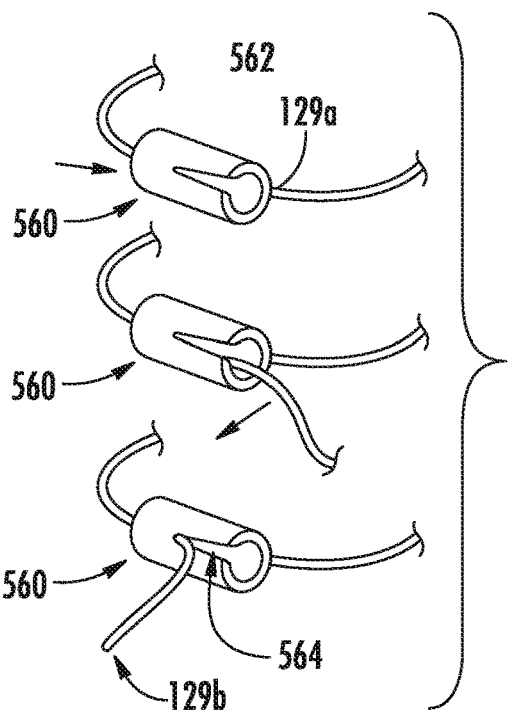
FIG. 25 illustrates yet another embodiment of a "feed and cinch" suture holding member.
Figure 26:
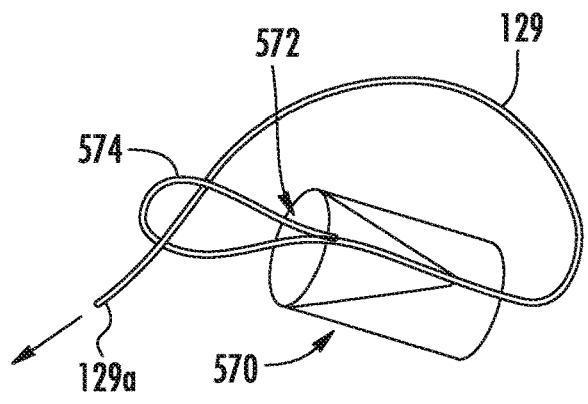
FIG. 26 illustrates a locking lasso embodiment of a suture holding member.

Referring now to FIGS. 24-26, additional embodiments of suture holding members that allow the user to feed one end of a suture therethrough and cinch it tight are provided. As shown in FIG. 24, a suture holding member 550 includes a trough 552 for receiving one end of the suture 129. Trough 552 may include a number of locking or friction resistance elements therein to hold suture 129 and prevent it from backing out of suture holding member 550. The other free end of suture 129 is suitably fixed to one end of suture holding member 550.

FIG. 25 illustrates a similar embodiment wherein a suture holding member 560 includes a channel 562 for receiving one free end 129b of suture 129. The other free end 129a is fixed to suture holding member 560. Channel 562 may further include a narrowed region 564 for cinching suture 129 therein.

FIG. 26 illustrates a locking lasso suture holding member 570 that includes an opening 572 for receiving one end of suture 129. In this embodiment, one end of suture 129 is formed into an open loop 574 and the other end of suture 129 is feed through loop 574 and then pulled to tighten loop 574 around suture 129 within suture holding member 570.

In yet another embodiments suture holding member can be designed as a cinch bead, a loop or similar structure. The suture has a length selected to allow the bowel to expand to its natural, unconstrained configuration with the free ends of the suture extending through the suture holding member. In one such embodiment, the free ends of the suture are coupled to each other (or designed as a loop such that there is no "free end") to ensure that the suture does not withdraw through the suture holding member. This allows the bowel to expand while ensuring that the suture will remain in position around the bowel and secure within the suture holding member.

Figure 27:
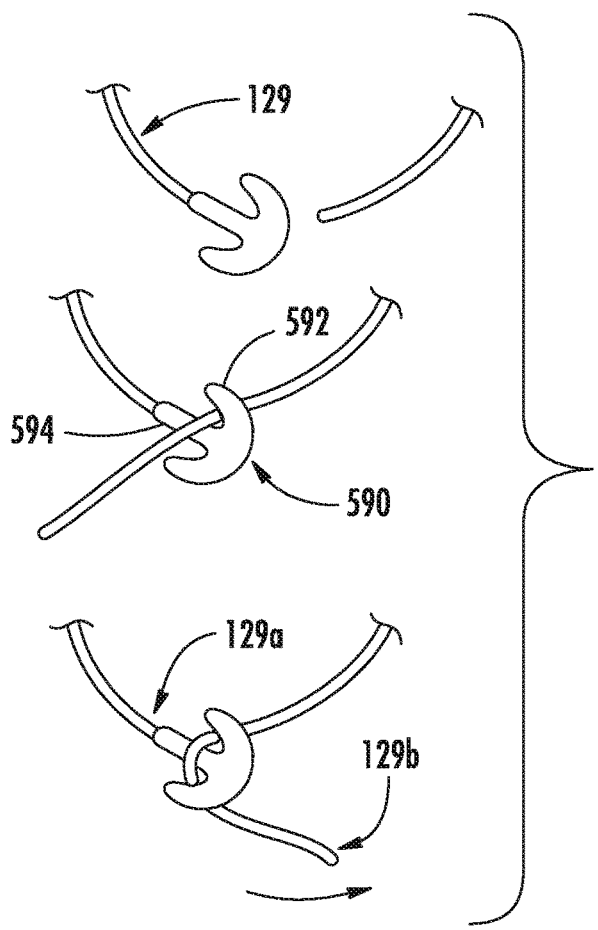
FIG. 27 illustrates a "wrap and cinch" anchor suture holding member.

Referring now to FIG. 27, another embodiment of a suture holding member 590 includes an anchor 592 for receiving one free end of suture 129, while the other free end is fixed to another end 594 of suture holding member 590. As shown, suture 129 may be wrapped around anchor 592 and then pulled to tighten suture 129 down and cinch the tissue.

Figure 28A:
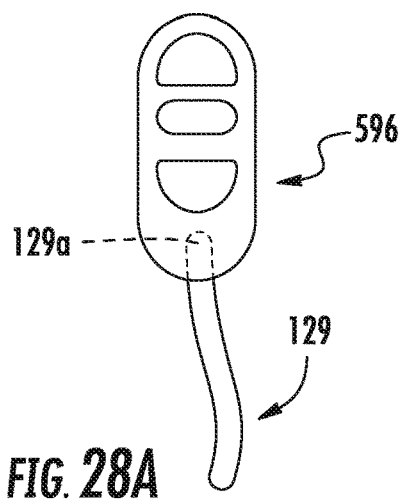
FIGS. 28A and 28B illustrate one-step feed suture holding members.
Figure 28B:
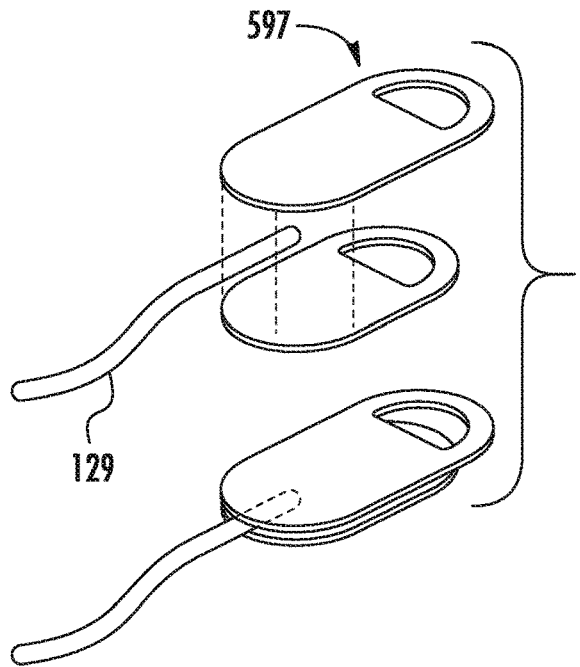

FIGS. 28A and 28B illustrate embodiments of a suture holding member that allow suture 129 to be fed into the suture holding member and locked with one simple step. FIG. 28A illustrates an example of a "soda tab" suture holding member 596. FIG. 28B illustrates an example of a "Double-D" suture holding member 597.

Of course it will be recognized by those skilled in the art that the devices disclosed herein are not limited to the specific embodiments of a suture holding member described above and shown in the representative drawings. For example, suture 129 may include direction elements, such as barbs (not shown), that allow the suture to be easily fed through a suture holding member in one direction while resisting movement of the suture in the opposite direction. Alternatively, the suture holding member may include elements similar to a zip tie that allow the user to easily pull suture through the zip tie, while resisting movement in the opposite direction.

Figure 29A:
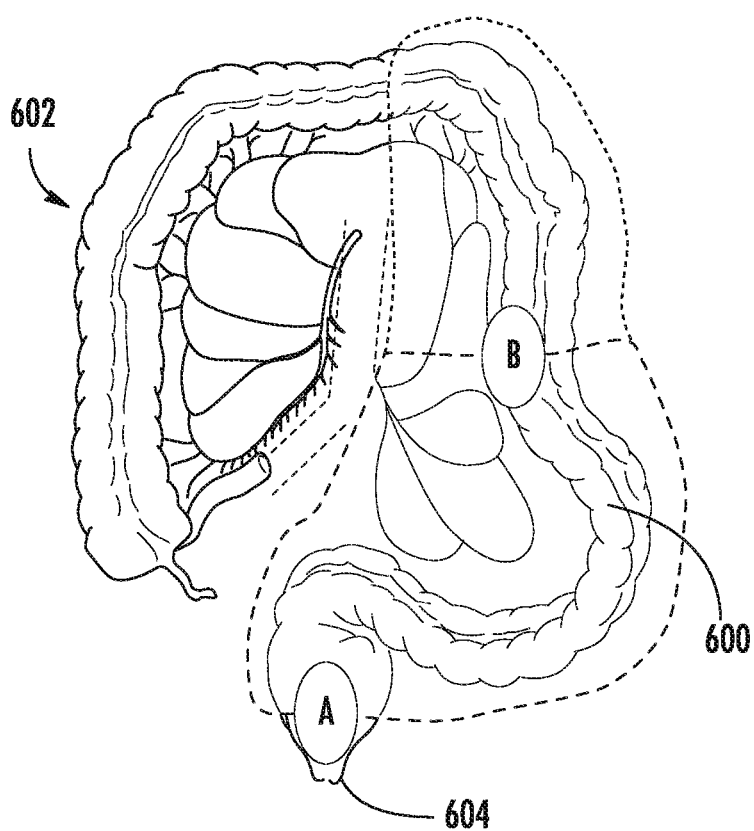
FIGS. 29A and 29B schematically illustrate a method of resecting tissue in a lower anterior resection (LAR) procedure.
Figure 29B:
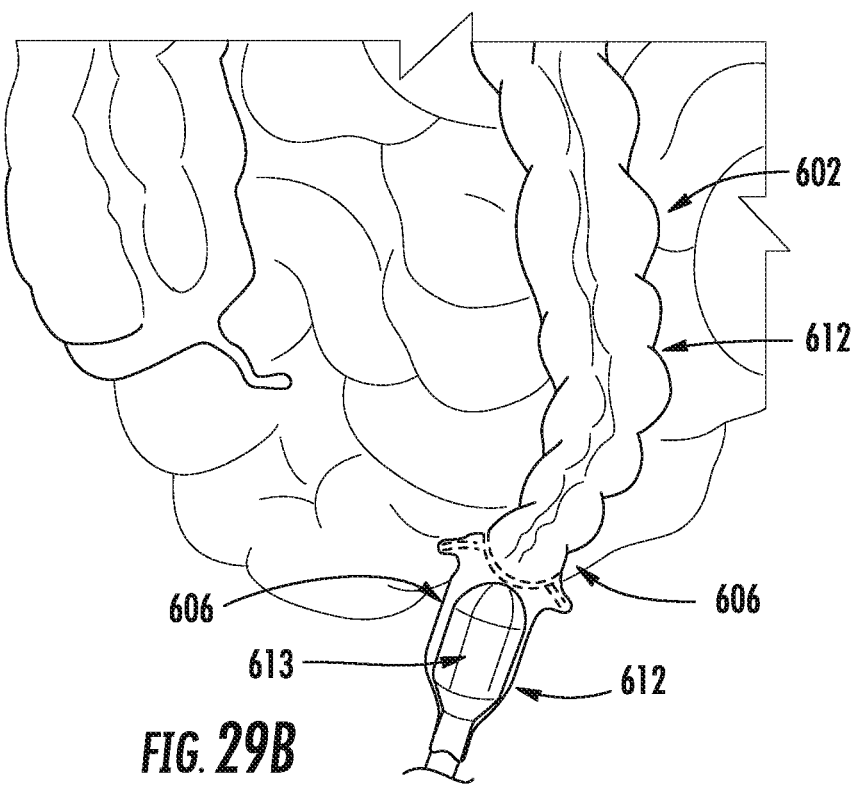
Figure 30:
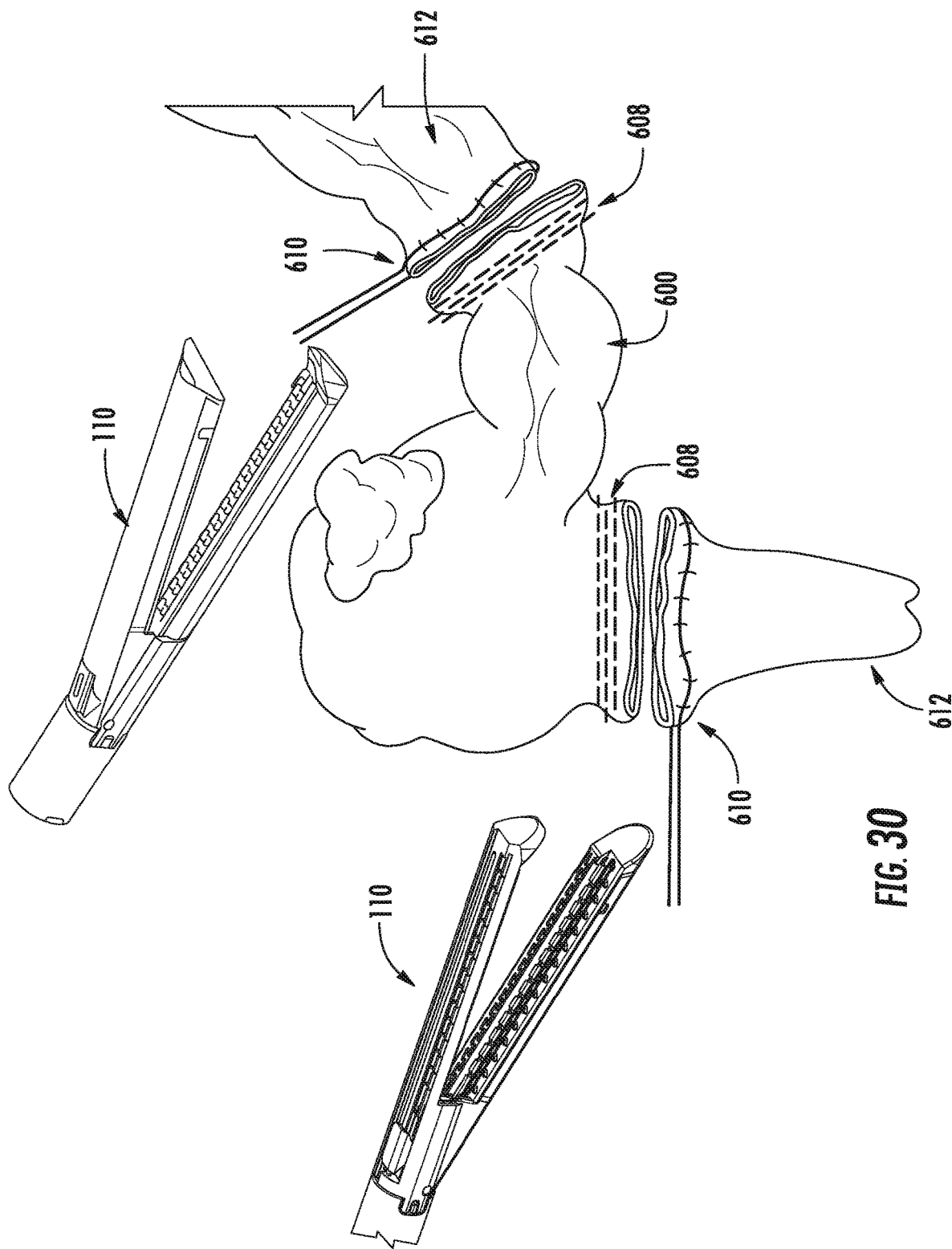
FIG. 30 schematically illustrates a linear staple line and a purse string staple hoop placed onto two sections of the bowel.

FIGS. 29-31 illustrate a method of resecting tissue during, for example, a lower anterior resection (LAR). In an LAR procedure, an unhealthy portion 600 of the intestines 602 near the rectum 604 is removed. As shown in FIGS. 29A and 29B, the portion from A to B will be removed and then the two remaining portions 612 will be brought together in an anastomosis 606.

As shown in FIG. 30, the surgeon typically dissects an unhealthy portion 600 of the bowel 602 and applies a linear staple line 608 across either end of the unhealthy portion 600 of the bowel to prevent its contents from spilling out during the procedure. In addition, the surgeon will place a staple line or a purse string hoop 610 on the healthy portions 612 of the bowel to cinch these portions closed until they are brought together during the anastomosis portion of the procedure. FIG. 30 also illustrates the ability to roll the instrument around to apply the purse string to the other side of the bowl 602. After the unhealthy portion 600 has been removed, a circular stapler 613 is advanced through the bowel 602 and the two remaining ends of the bowel are drawn together so that they can be joined in an anastomosis 606 with the circular stapler 613 (see FIG. 29B).

According to one method, a surgical instrument such as one of the instruments described above, is used to place the linear staple line 608, dissect the bowel and place a purse string suture hoop 610 around the other portion of the bowel 602 near the distal stump of the rectum. FIGS. 31A and 31B illustrate one portion of this procedure, wherein a purse string suture hoop 610 is placed around the healthy portion 612 of the bowel 602. As shown, surgical instrument 100 is maneuvered in place such that jaws 111, 112 are placed around the tissue 612. As the jaws 111, 112 are closed, drive member 150 is translated distally to engage the various staple pushers within end effector 110 and dissect the tissue along knife cutting edge 151, as discussed above. The staple pushers drive linear staples 124 into tissue on one side of the cutting edge 151 (not shown) and purse string staples 127a, 127b into the tissue on the other side of the cutting edge.

As shown in FIG. 31A, staples 127a are driven into the top portion of tissue 612 and staples 127b are driven into the bottom portion of tissue 612 to ensure that the entire circular cross-section of the bowel has staples therearound. At the same time, suture 129 is placed between staples 127a, 127b and the bowel tissue such that a purse string suture hoop 610 is formed around the bowel. Suture 129 includes an open loop 630 that is connected to the top and bottom portions of suture, and free ends 129a, 129b that pass through suture holding member 500. With this design, suture holding member 500 is facing the instrument (and the user), thereby making it much easier for the user to visualize the suture holding member 500 and cinch the bowel.

As shown in FIG. 31B, once the purse string suture hoop 610 has been placed around the bowel, the surgeon can easily grab the two fee ends 129a, 129b of suture 129 and pull. As the free ends 129a, 129b are pulled away from suture holding member 500, suture holding member 500 provides the necessary tension to bowel 612 to cinch it closed. The open loop 630 of suture 129 is pulled through staples 127a, 127b until it has tightened around the bowel 612. At this point, further pulling of the free ends 129a, 129b begins to cinch the bowel closed. The surgeon can then tie a knot in the free ends of suture, or tighten suture 129 using other methods described above to close the bowel until the surgeon has resected the unhealthy tissue and is ready to complete the anastomosis.

The unique features of surgical instrument 100 described above provide a wider tissue cuff 650 between the line of dissection 652 and the purse string suture hoop 610. The more "tissue cuff" that can be achieved, the more likely that there will be tissue within the purse string hoop as it is drawn closed. In addition, increasing the width of the tissue cuff 650 between the purse string sutures 127a, 127b and the transection plane 652 facilitates the user drawing the purse string hoop 610 closed and minimizes complications with the circular stapler performing the anastomosis.

While several embodiments have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical stapling instrument, comprising:
   an elongate shaft having a longitudinal axis, a distal end, and a proximal end;
   an end effector coupled to the distal end of the shaft and comprising first and second jaws configured to move between open and closed positions;
   a first row of staples in each of the first and second jaws;
   a second row of staples in the second jaw on an opposite side of the longitudinal axis from the first row of staples;
   a suture extending through the first row of staples; and
   a drive member configured to translate distally through the end effector to drive the first and second row of staples into tissue such that the suture is disposed between the first row of staples and the tissue.

2. The surgical stapling instrument of claim 1, further comprising a cutting element coupled to the drive member and configured to dissect tissue as the drive member translates distally through the first and second jaws, wherein the second row of staples comprises at least two rows of linear staples.

3. The surgical stapling instrument of claim 2, wherein the first and second jaws each have a tissue contacting surface, wherein a distance between the first row of staples and the cutting element along the tissue contacting surfaces is greater than a distance between the second row of staples and the cutting element.

4. The surgical stapling instrument of claim 3, wherein the cutting element is disposed laterally from the longitudinal axis on an opposite side from the first row of staples.

5. The surgical stapling instrument of claim 3, wherein the first row of staple is oriented at a transverse angle relative to the longitudinal axis of the shaft.

6. The surgical stapling instrument of claim 3, wherein the instrument defines an upper portion and a lower portion, wherein the first and second jaws each comprise a tissue contacting surface having an angled portion that extends downwardly from a first axis to a second axis closer to the lower portion of the shaft than the first axis.

7. The surgical stapling instrument of claim 6, wherein the angled portion of the tissue contacting surfaces extends downwardly from the cutting element towards the first row of staples.

8. The surgical stapling instrument of claim 1, wherein the drive member is configured to drive the first row of staples into tissue such that the suture, in combination with the staples, forms a purse string with the tissue.

9. The surgical stapling instrument of claim 1, wherein the first row of staples in the first jaw is offset along the longitudinal axis from the first row of staples in the second jaw.

10. The surgical stapling instrument of claim 1, wherein each staple in the first row of staples in the first jaw is positioned longitudinally between two of the staples in the first row of staples in the second jaw.

11. The surgical stapling instrument of claim 1, further comprising a suture holding member within the end effector, wherein at least the first end of the suture is coupled to the holding member.

12. A surgical stapling instrument comprising:
   an elongate shaft having a longitudinal axis, a distal end, and a proximal end;
   an end effector coupled to the distal end of the shaft and having first and second jaws configured to move between open and closed positions;
   a row of staples in each of the first and second jaws;
   a suture extending through each row of staples, the suture having first and second free ends;
   a suture holding member within the end effector, wherein at least the first free end of the suture is coupled to the suture holding member; and
   a drive member configured to translate distally through the first and second jaws to drive the row of staples into tissue such that the suture extends between the staples and the tissue.

13. The surgical stapling instrument of claim 12, wherein the first and second free ends of the suture extend through the suture holding member.

14. The surgical stapling instrument of claim 13, wherein the first and second free ends of the suture extend through openings in the suture holding member, and wherein the suture is movable relative to the suture holding member.

15. The surgical stapling instrument of claim 14, wherein the tissue is a bowel tissue having a diameter in an unconstrained configuration, and wherein the suture has a length selected to allow the bowel tissue to expand to the diameter in the unconstrained configuration with the first and second free ends extending through the suture holding member.

16. The surgical stapling instrument of claim 12, wherein the suture holding member has a tissue contacting surface, and a second surface opposite the tissue contacting surface; and wherein the suture holding member is disposed within the end effector such that the second surface faces a distal end of the end effector when the row of staples have been driven into the tissue.

17. The surgical stapling instrument of claim 12, further comprising a channel in each of the first and second jaws for receiving a portion of the suture.

18. The surgical stapling instrument of claim 17, wherein the suture holding member is disposed proximal to the row of staples, the suture extending from the suture holding member through the row of staples in the first jaw, through the channel in the first jaw, through the channel in the second jaw and through the row of staples in the second jaw such that the second free end is disposed proximally of the row of staples.

19. The surgical stapling instrument of claim 18, wherein the suture forms a substantially U-shape in each of the first and second jaws.

20. The surgical stapling instrument of claim 12, wherein the suture is coupled to the suture holding member with a friction fit configured to release under a threshold level of tension.

* * * * *